United States Patent
McIntyre et al.

(10) Patent No.: US 11,291,832 B2
(45) Date of Patent: Apr. 5, 2022

(54) PATIENT-SPECIFIC LOCAL FIELD POTENTIAL MODEL

(71) Applicant: Case Western Reserve University, Cleveland, OH (US)

(72) Inventors: Cameron McIntyre, Lakewood, OH (US); Nicholas Maling, Cleveland, OH (US); Scott Lempka, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 217 days.

(21) Appl. No.: 16/397,141

(22) Filed: Apr. 29, 2019

(65) Prior Publication Data

US 2020/0001071 A1 Jan. 2, 2020

Related U.S. Application Data

(60) Provisional application No. 62/692,064, filed on Jun. 29, 2018.

(51) Int. Cl.
*A61N 1/05* (2006.01)
*A61N 1/36* (2006.01)
(Continued)

(52) U.S. Cl.
CPC ....... *A61N 1/0534* (2013.01); *A61N 1/36064* (2013.01); *A61N 1/36082* (2013.01);
(Continued)

(58) Field of Classification Search
CPC .............. A61N 1/0534; A61N 1/36064; A61N 1/36082; A61N 1/36185; G16H 20/30
(Continued)

(56) References Cited

U.S. PATENT DOCUMENTS 8,606,360 B2 * 12/2013 Butson ................... A61B 5/407
607/45
2005/0228250 A1 * 10/2005 Bitter ................. A61B 5/02007
600/407

(Continued)

OTHER PUBLICATIONS

Lempka, Scott & Mcintyre, Cameron. (2013). Theoretical Analysis of the Local Field Potential in Deep Brain Stimulation Applications. PloS one. 8. e59839. 10.1371/journal.pone.0059839.*

*Primary Examiner* — Carl H Layno
*Assistant Examiner* — Michael J Lau
(74) *Attorney, Agent, or Firm* — Eschweiler & Potashnik, LLC

(57) ABSTRACT

Embodiments discussed herein facilitate identification of a target area within a region of a brain for stimulation via one or more BS (Brain Stimulation) electrodes. One example embodiment comprises generating, based on radiological imaging of a region of a brain of a patient and BS electrode lead(s), a patient-specific anatomical model of the region and lead(s); populating the patient-specific anatomical model with neuron models based on associated neuronal densities of at least one of the region or one or more sub-regions of the region; constructing a patient-specific local field potential (LFP) model of the region based on the patient-specific anatomical model and location(s)/orientation(s) of the one or more BS electrode leads; and identifying, via the patient-specific LFP model of the region, a target area within the region for at least one of monitoring or treatment of a medical condition via the one or more BS electrode leads.

20 Claims, 9 Drawing Sheets

(51) Int. Cl.
  *G16H 20/30*  (2018.01)
  *A61B 5/055*  (2006.01)
  *A61B 5/00*   (2006.01)
(52) U.S. Cl.
  CPC .............. *A61B 5/055* (2013.01); *A61B 5/4064* (2013.01); *A61N 1/36185* (2013.01); *G16H 20/30* (2018.01)
(58) Field of Classification Search
  USPC .......................................................... 607/45
  See application file for complete search history.

(56) References Cited

U.S. PATENT DOCUMENTS

| | | | | |
|---|---|---|---|---|
| 2007/0203543 A1* | 8/2007 | Stone | .................. | A61N 1/37247 607/59 |
| 2007/0203544 A1* | 8/2007 | Goetz | ................ | A61N 1/37247 607/59 |
| 2007/0203545 A1* | 8/2007 | Stone | .................... | G16H 50/50 607/59 |
| 2007/0203546 A1* | 8/2007 | Stone | ................. | A61N 1/37247 607/59 |
| 2008/0123922 A1* | 5/2008 | Gielen | ................ | A61B 6/5241 382/131 |
| 2008/0125833 A1* | 5/2008 | Bradley | ............... | A61N 1/3605 607/60 |
| 2011/0054583 A1* | 3/2011 | Litt | .................... | A61B 5/14552 607/116 |
| 2011/0264165 A1* | 10/2011 | Molnar | ............... | A61N 1/36185 607/45 |
| 2013/0053922 A1* | 2/2013 | Ahmed | .............. | A61N 1/36103 607/45 |
| 2013/0085361 A1* | 4/2013 | Mercanzini | .............. | A61B 5/24 600/377 |
| 2013/0268019 A1* | 10/2013 | Gupta | ................ | A61N 1/36164 607/45 |
| 2015/0112403 A1* | 4/2015 | Ruffini | ............... | A61N 1/36025 607/45 |
| 2015/0134031 A1* | 5/2015 | Moffitt | ............... | A61N 1/36185 607/62 |
| 2015/0157858 A1* | 6/2015 | McIntyre | ........... | A61N 1/36139 607/45 |
| 2015/0246233 A1* | 9/2015 | Kaemmerer | ....... | A61N 1/36139 607/59 |
| 2016/0055304 A1* | 2/2016 | Russell | .............. | A61N 1/36034 705/3 |
| 2016/0081577 A1* | 3/2016 | Sridhar | .................. | A61B 5/742 600/383 |
| 2017/0120054 A1* | 5/2017 | Moffitt | ................. | A61N 1/0534 |
| 2017/0251943 A1* | 9/2017 | Petersson | .............. | A61B 5/7257 |

* cited by examiner

US 11,291,832 B2

PATIENT-SPECIFIC LOCAL FIELD POTENTIAL MODEL

CROSS REFERENCE TO RELATED APPLICATIONS

This application claims the benefit of U.S. Provisional Patent Application No. 62/692,064 filed Jun. 29, 2018, entitled "PATIENT-SPECIFIC LOCAL FIELD POTENTIAL MODEL", the contents of which are herein incorporated by reference in their entirety.

FEDERAL FUNDING NOTICE

This invention was made with government support under the grant(s) R01 MH106173 and R01 NS086100, awarded by the National Institutes of Health. The government has certain rights in the invention.

BACKGROUND

Clinical brain stimulation (BS) technology (e.g., Deep Brain Stimulation (DBS), etc.) is evolving to enable chronic recording of local field potentials (LFPs) that represent electrophysiological biomarkers of an underlying disease state. BS electrodes can be used to treat a variety of conditions, such as dystonia, epilepsy, essential tremor, obsessive-compulsive disorder, Parkinson's disease, etc. However, little is known about the biophysical basis of LFPs, or how the patient's unique brain anatomy and electrode placement impact recordings via the BS electrodes.

BRIEF DESCRIPTION OF THE DRAWINGS

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

DETAILED DESCRIPTION

Various embodiments can employ techniques discussed herein for identification of a target area of a brain region for monitoring and/or stimulation via one or more BS (Brain Stimulation) electrodes based on a patient-specific LFP (Local Field Potential) model of the brain region of the patient. Embodiments discussed herein can provide accurate modeling of patient-specific neuroanatomy and how it interacts with implanted BS electrodes, and can thereby facilitate determination of how (e.g., at what stimulation amplitude), when (via identifying of the relevant target area, such that it can be monitored via BS electrode(s)), and where (via identification of the relevant target area, as well as which BS electrodes can best stimulate the target area) to stimulate the target area via BS electrodes.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic or circuit, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 1:
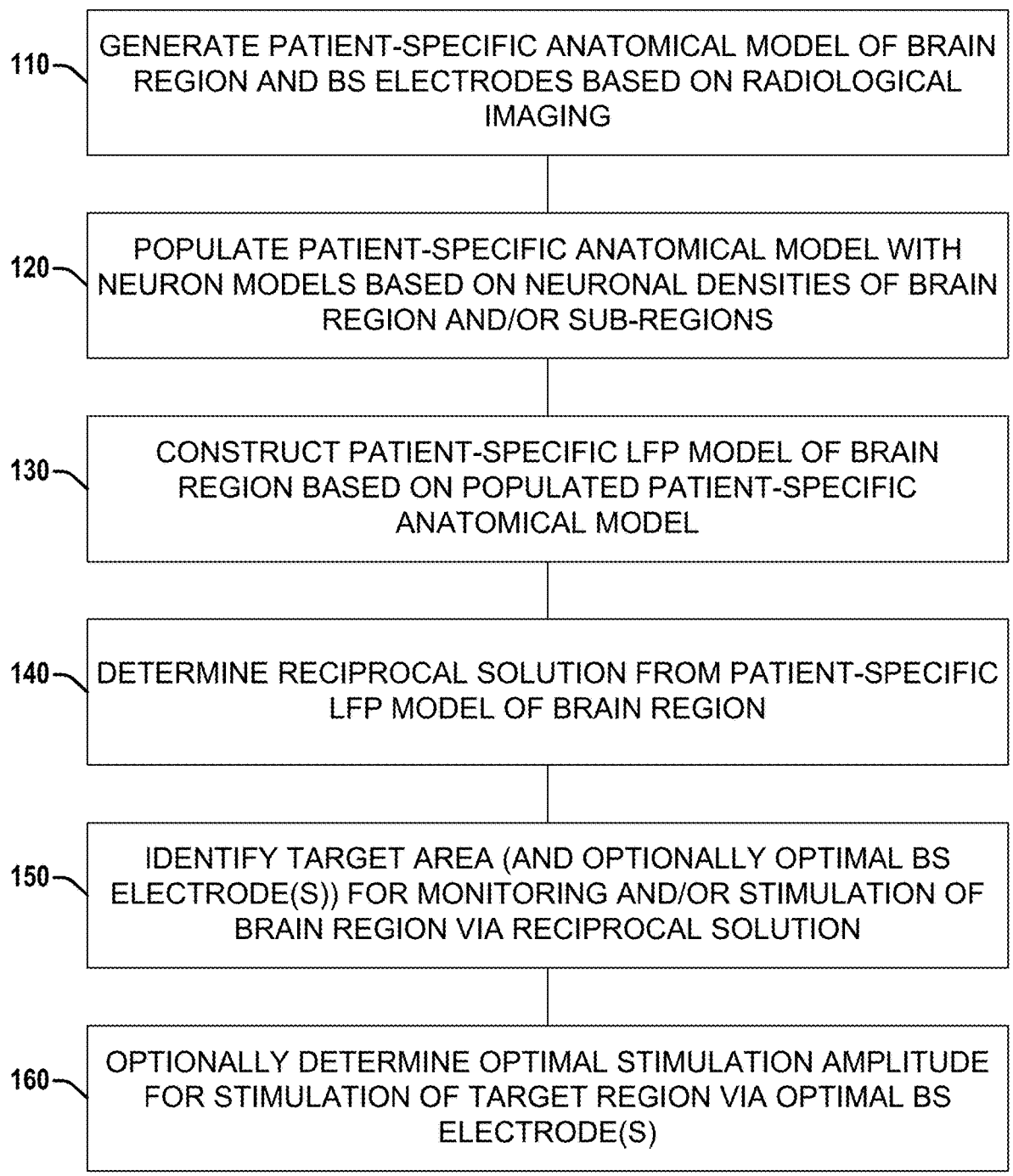
FIG. 1 illustrates a diagram of a first example flow of a method or set of operations that that facilitates identification of a target area of a brain region or nucleus for BS (Brain Stimulation) electrode monitoring and/or stimulation, according to various embodiments discussed herein.

Various embodiments can employ techniques discussed herein to facilitate determination of a target area of a brain region or nucleus for monitoring and/or stimulation via one or more BS (Brain Stimulation) electrodes via a patient-specific model constructed based on patient-specific neuroanatomy, BS electrode location(s), and modeled reconstructions of individual neurons in the brain region/nucleus. Referring to FIG. 1, illustrated is a diagram showing a first example flow of a method or set of operations 100 that facilitates identification of a target area of a brain region or nucleus for BS electrode monitoring and/or stimulation, according to various embodiments discussed herein.

The set of operations 100 can comprise, at 110, generating a patient-specific anatomical model of a brain region and one or more BS electrodes in or near the brain region based on radiological imaging. The radiological imaging can comprise pre-operative imaging (e.g., magnetic resonance imaging (MRI), etc.) of the brain region prior to implantation of BS electrodes that can provide greater anatomical detail regarding the brain region, which can be used, for example, to determine the relative size and positioning of the brain region and/or sub-regions of the brain region The radiological imaging can also comprise post-operative (e.g., computed tomography (CT), etc.) imaging after implantation of the BS electrodes that can show the position and orientation of the BS electrodes relative to the brain region. In various embodiments, the post-operative imaging can be co-registered to the pre-operative imaging to provide detailed information on the brain region and the position and orientation of the BS electrodes relative to the brain region. Based on this information, a model of the brain region, comprising any relevant sub-regions, can be created, and can comprise modeled BS electrodes with positions and orientations corresponding to that determined from radiological imaging.

The set of operations can further comprise, at 120, populating the patient-specific anatomical model with individual neuron models based on the neuronal densities of the brain region and the sub-regions. The total number of individual neuron models populated in the brain region and/or each sub-region of the model can approximate the total number of neurons in that brain region and/or each sub-region as estimated based on the volumes of the brain region and/or each sub-region as determined based on the radiological imaging and based on known neuronal densities for the brain region and/or each sub-region. Additionally, in various embodiments, the populated neuronal models can have modeled properties conforming to measured properties of neurons from the brain region and/or each sub-region (e.g., number of synaptic inputs, etc.). In some embodiments, neuron models can employ relatively simple models such as point neurons, which can improve computational efficiency, while in other embodiments, more complicated neuron models (e.g., multi-compartment neurons as discussed in the example use case, etc.) can be employed, which can provide improved accuracy, but are more computationally intensive.

The set of operations 100 can further comprise, at 130, constructing a patient-specific LFP (local field potential) model of the brain region based on the populated patient-specific anatomical model. The LFP model can comprise an electrical source model comprising the populated neuron models at their associated locations (e.g., evenly distributed through the brain region and/or each sub-region based on the associated densities, etc.) and a volume conductor model that can model conduction through the brain region and/or each sub-region, as well as in the vicinity of the BS electrodes.

The set of operations 100 can further comprise, at 140, determining a reciprocal solution from the patient-specific LFP model of the brain region. A unit current source can be placed at each BS electrode in turn to determine the voltage at locations (e.g., finite element model (FEM) nodes) in the patient-specific LFP model, which, by the theorem of reciprocity, is also the voltage that would be generated at that BS electrode for a unit current. Based on this, contributions to a waveform from individual neuron models of the patient-specific LFP model can be calculated.

The set of operations 100 can further comprise, at 150, identifying, based on the reciprocal solution, a target area in the brain region for monitoring and/or stimulation via at least one of the BS electrodes. Additionally, 150 can further comprise identifying at least one of the BS electrodes that is more effective than other BS electrodes for monitoring and/or stimulation of the target area. In various embodiments, identifying the target area can comprise identifying a size, location, and/or shape of the target area. In some embodiments, to simplify analysis and improve computational efficiency, the target area can be assumed to have a predetermined shape (e.g., spherical, such that the location can be defined via a location of the center independent of orientation, and the size can be defined via a single parameter, radius), which, although not entirely accurate, may be sufficiently accurate for various clinical applications (e.g., monitoring and/or treatment of an associated medical condition) and also more computationally efficient. In various embodiments, identifying the target area can comprise determining a best area with respect to a fitness metric, wherein the fitness metric can be based on at least one of a shape of a power spectrum or a distribution of power in a relevant frequency band (e.g., low, such as beta band, high, etc.) for treatment of the medical condition.

The set of operations 100 can optionally further comprise, at 160, determining, based on the reciprocal solution, one or more stimulation amplitudes for treatment of the medical condition via at least one of the BS electrodes. In embodiments comprising 160, based on the reciprocal solution, one or more stimulation amplitudes can be determined that, if applied by at least one BS electrode, can produce a waveform from the target area that can mitigate symptoms (e.g., tremors, seizures, etc.) of an underlying medical condition. Additionally, various embodiments can further comprise applying the identified stimulation amplitude(s) via at least one of the BS electrodes, which can occur based on monitoring via at least one of the BS electrodes (e.g., when monitoring determines a waveform from the target area is associated with one or more symptoms that can be mitigated via stimulation, etc.).

Figure 2:
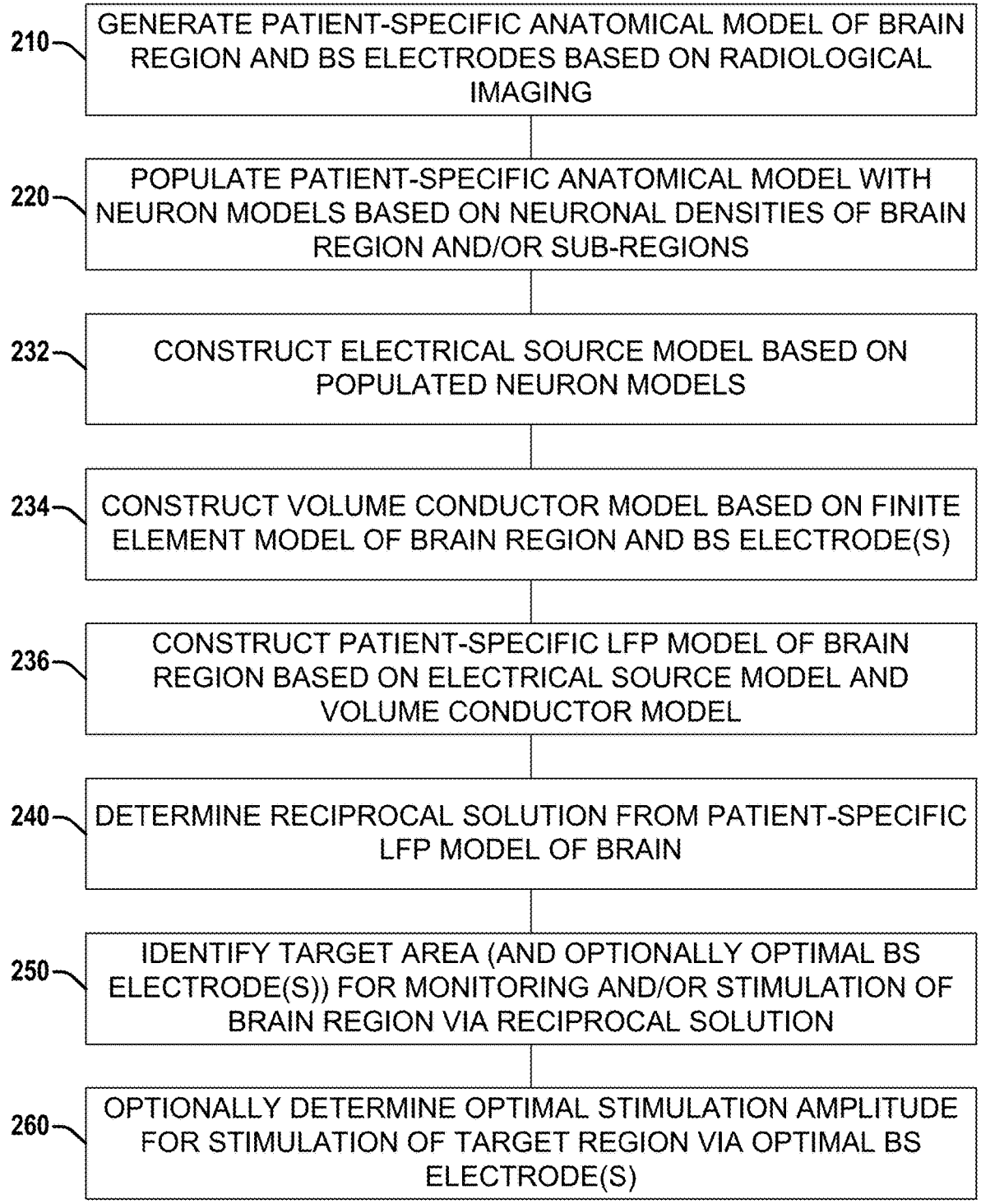
FIG. 2 illustrates a diagram of a second example flow of a method or set of operations that that facilitates identification of a target area of a brain region or nucleus for BS electrode monitoring and/or stimulation, according to various embodiments discussed herein.

Referring to FIG. 2, illustrated is a diagram showing a second example flow of a method or set of operations 200 that facilitates identification of a target area of a brain region or nucleus for BS electrode monitoring and/or stimulation, according to various embodiments discussed herein. Method or set of operations 200 is similar to method or set of operations 100, but can include additional and/or alternative operations and/or features.

The set of operations 200 can comprise, at 210, 220, and 240 through 260, operations substantially similar to operations 110, 120, and 140 through 160 of set of operations 100. However, in place of 130 in set of operations 100, set of operations 200 can comprise 232-236.

At 232, an electrical source model can be constructed based on the populated neuron models of the patient-specific anatomical model from 220. Depending on the specific neuron models (e.g., point, multi-compartment, etc.), the specific details of the electrical source model can vary. Additionally, various details can be selected based on the specific neuroanatomy of the brain region (e.g., number of synaptic inputs, etc.). Inputs can vary between individual neuron models, and can be, for example, synchronous or asynchronous in a relevant frequency band (e.g., high or low, etc.).

At 234, a volume conductor model can be constructed to model the brain tissue in the brain region, BS electrodes, and region surrounding the BS electrodes (e.g., to model tissue encapsulation). The volume conductor model can be a FEM (Finite Element Model) model conductivity of the brain tissue (e.g., gray matter typically has an isotropic conductivity around 0.2 S/m, etc.), tissue capsule interface, and BS electrodes.

At 236, a patient-specific LFP model of the brain region and BS electrodes can be constructed by combining the electrical source model of 232 with the volume conductor to create a patient-specific LFP model of the brain region.

Techniques and aspects of various embodiments are further explained below, in connection with an example use case that evaluates DBS (Deep Brain Stimulation) electrode placement in connection with patient-specific anatomy of the STN (Subthalamic Nucleus) to facilitate improved treatment of Parkinson's disease via patient-specific data informing when, where, and how to activate DBS electrodes to minimize symptoms, as well as additional example embodiments.

Example Use Case: Biophysical Basis of Subthalamic Local Field Potentials Recorded from Deep Brain Stimulation Electrodes Clinical deep brain stimulation (DBS) technology is evolving to enable chronic recording of local field potentials (LFPs) that represent electrophysiological biomarkers of the underlying disease state. However, little is known about the biophysical basis of LFPs, or how the patient's unique brain anatomy and electrode placement impact the recordings. Therefore, a patient-specific computational framework to analyze LFP recordings within a clinical DBS context was developed. A subject with Parkinson's disease implanted with a Medtronic Activa PC+S DBS system was selected, and their subthalamic nucleus (STN) and DBS electrode location was reconstructed using medical imaging data. The patient-specific STN volume was populated with 235,280 multi-compartment STN neuron models, providing a neuron density consistent with histological measurements. Each neuron of the neuron model received time varying synaptic inputs and generated transmembrane currents that gave rise to the LFP signal recorded at DBS electrode contacts residing in a finite element volume conductor model. The model was then used to study the role of synchronous beta-band inputs to the STN neurons on the recorded power spectrum. Three bipolar pairs of simultaneous clinical LFP recordings were used in combination with an optimization algorithm to customize the neural activity parameters in the model to the patient. The optimized model predicted a 2.4 mm radius of beta-synchronous neurons located in the dorsolateral STN. These theoretical results enabled biophysical dissection of the LFP signal at the cellular-level with direct comparison to the clinical recordings, and the model system provides a scientific platform to help guide the design of DBS technology focused on using subthalamic beta activity in closed-loop algorithms.

The analysis of DBS LFP data is rapidly expanding from scientific curiosity to the basis for clinical biomarkers capable of improving the therapeutic efficacy of stimulation. With this growing clinical importance comes a growing need to understand the underlying electrophysiological fundamentals of the signals and the factors contributing to their modulation. The model of the example embodiment of this use case (like other embodiments) reconstructs the clinical LFP from first principles and highlights the importance of patient-specific factors in dictating the signals recorded.

Subthalamic deep brain stimulation (DBS) is an established clinical therapy for advanced Parkinson's disease (PD). Over the last two decades, subthalamic DBS surgeries have provided unique experimental opportunities to record electrophysiological activity from subthalamic nucleus (STN) neurons in thousands of patients with PD. This wealth of data has provided valuable insights on the pathophysiology of PD and highlighted the possible role of excessive STN neural synchrony in the generation of PD symptoms. In particular, local field potential (LFP) recordings from DBS macroelectrode contacts represent an established platform for detecting and analyzing neural synchrony in PD.

Chronic LFP recordings from DBS electrodes in the STN are currently the focus of wide ranging clinical research studies. The ability to obtain chronic recordings facilitates the possible use of LFPs as clinical biomarkers in closed-loop control systems, which have become a driving force in the development of commercial DBS technology. Specifically, beta band (12-30 Hz) activity has received the greatest attention in PD research because of its correlative association with PD symptoms. As such, LFP recordings of STN beta activity represent viable control signals for adaptive subthalamic DBS systems in humans.

While the scientific and clinical utility of STN LFPs is already well established, numerous questions on the basic biophysics of these signals remain unanswered by existing analysis and techniques. For example, how many STN neurons contribute to the clinical beta signal? What is the degree of synaptic synchrony necessary to create the beta signal? Where are the synchronized neurons located within the STN? Experimentalists have attempted to address some of these questions by coupling microelectrode recordings of single units in the STN with macroelectrode LFP results. Even still, it is currently impossible to individually and simultaneously record from the huge number of neurons responsible for the LFP signal. To address this gap in scientific knowledge, advanced computational modeling methods can be employed for simulating LFPs. LFP simulations are capable of explicitly representing thousands of anatomically and electrically realistic neuron models, as well as their individual synaptic inputs. These neural source models can be coupled to volume conductor electric field models to then calculate the voltage recorded by the electrode. This computational modeling approach can enable detailed dissection of the underlying biophysics of the LFP signal.

First generation STN LFP models have provided some generalized results on the basic relationships between STN neural synchrony and the spatial extent of the recording volume. However, those initial analyses relied on spherical populations of uniformly distributed STN neurons perfectly centered around the DBS electrode. In reality, the STN is a complex 3D volume, where the density of neurons varies throughout the nucleus (for example, as shown in Table 1, below), and the DBS electrodes intersect the nucleus at an oblique angle. As such, each electrode contact is surrounded by a different density and distribution of neurons with different firing characteristics, and these details are likely to play an important role in the recorded signals. Therefore, a patient-specific STN LFP modeling framework was developed, and the simulated LFPs were directly compared to clinical LFP recordings from the patient. Given multiple simultaneous recording pairs from the DBS electrode, it was possible to define a theoretically optimal location and radius of beta synchrony within the STN LFP model that best matched the clinical recordings. The optimized model predicted the origin of beta synchrony to be in the dorsolateral STN, as numerous previous clinical analyses have also concluded. However, the model also offers the first quantitative estimate of the spatial extent of that recording volume, the number of neurons responsible, and their synaptic input characteristics. These results enhance the ability to interpret clinical LFP recordings at the cellular level, and provide scientific guidance for the design and implementation of DBS technology focused on using subthalamic beta activity in closed-loop algorithms.

Methods

A goal of this use case was to build an anatomically and electrically accurate model of LFPs recorded from DBS electrodes implanted in the human STN. A patient-specific model was created that was based on a male subject (age=52) diagnosed with tremor-dominant Parkinson's disease (disease duration=4 years) and implanted with an Activa PC+S DBS system (Medtronic Inc., Minneapolis, Minn.). The subject was selected from an ongoing clinical investigation at Stanford University, and for this use case, the STN on the right side of his brain was studied. The subject had an excellent response to DBS treatment, with the lateralized Unified Parkinson's Disease Rating Scale dropping from a pre-operative score of 20 to 2 at the 1-year follow-up. Throughout his first 3 years of DBS, monopolar stimulation was delivered exclusively from contact 1. Use of the Activa PC+S system facilitated obtaining chronic LFP recordings from the DBS electrodes. The example clinical LFP data used was acquired at the 1-month post-operative follow-up visit. Given that the analysis employed for this use case was performed at a single time point, it should be noted that the optimized model parameters fit to this patient might not share the same parameters that would be seen in the long-term chronic condition, and in various other embodiments, model parameters can be based on analysis performed over two or more points in time, or can be altered over time based on later analysis. This project was reviewed and approved by both the Case Western Reserve University and Stanford University institutional review boards.

Figure 3:
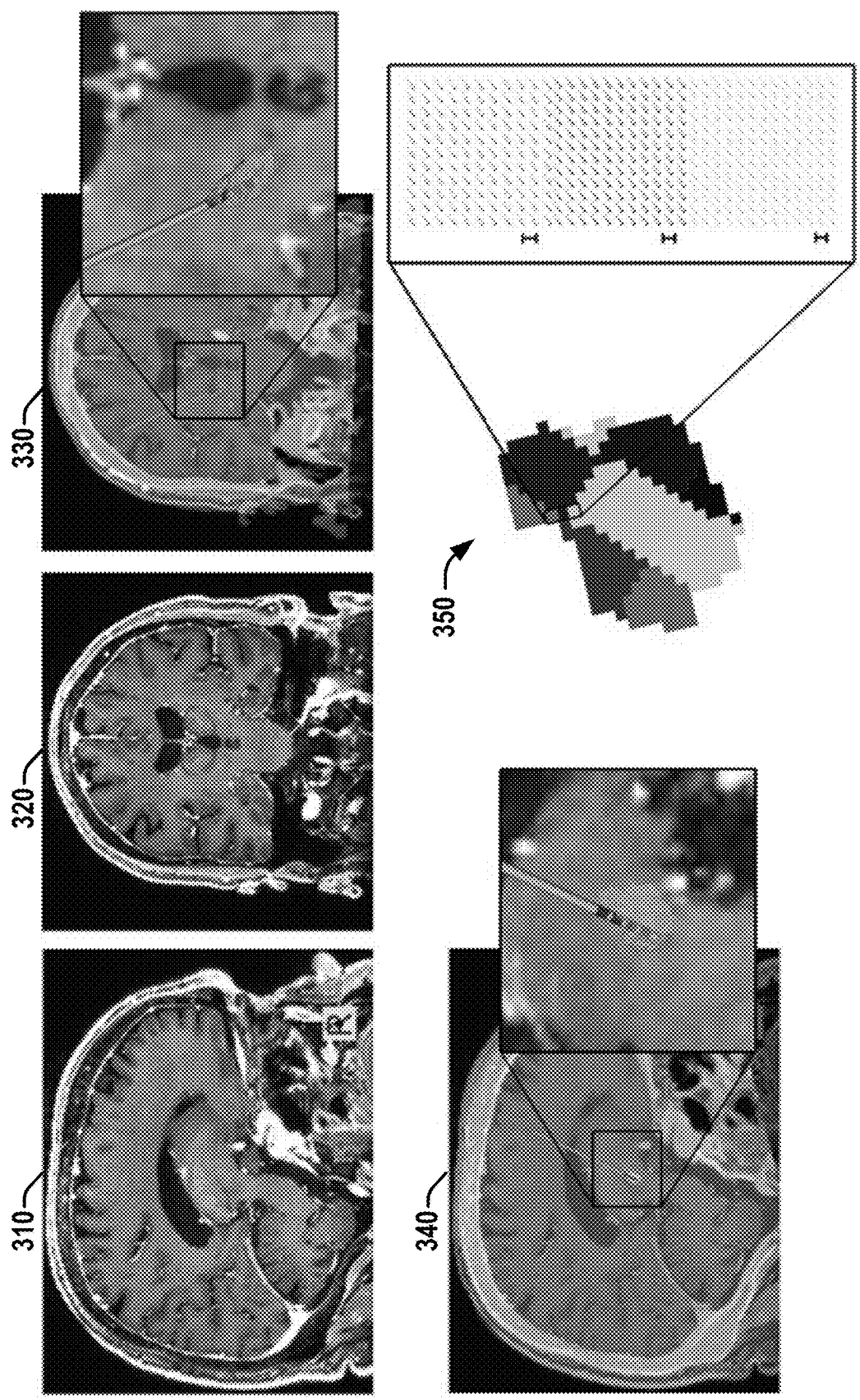
FIG. 3 illustrates a series of images showing the anatomical model employed in an example use case involving DBS (Deep Brain Stimulation) electrodes for STN (Subthalamic Nucleus) stimulation, according to various aspects discussed herein.

Anatomical Model:

The patient-specific anatomical model for this example use case was based on CT and MRI data acquired from the patient as part of their standard of care for DBS surgery. A preoperative T1-weighted MRI was used as the anatomical basis for the overall model. Referring to FIG. 3, illustrated is a series of images showing the anatomical model employed in the example use case involving DBS (Deep Brain Stimulation) electrodes for STN (Subthalamic Nucleus) stimulation, according to various aspects discussed herein. In FIG. 3, images 310 and 320 show the preoperative MRI (Magnetic Resonance Imaging) and 3D brain at last fit to the patient, showing the thalamus and the STN. Images 330 and 340 show the post-operative CT (Computed Tomography) co-registered to the MRI of 310 and 320 and used to define the DBS lead location, visible in 330 and 340 as the diagonal shaft and striped contacts. At 350, the STN volume determined based on 310-340 is shown divided into 9 sectors that represented different regions of neuron cell density, as shown in Table 1, below. Each voxel in the STN volume was populated with grid points for the locations of STN neuron cell bodies for modeling the STN.

To define the location and position of the STN in the subject, a 3D volume estimate of the elderly STN placed within the MNI152 space was relied on. The Harvard-Oxford MNI152 brain atlas (https://fsl.fmrib.ox.ac.uk/fsl/fslwiki/Atlases), consisting of volumetric representation of several basal ganglia nuclei, was then fit to the patient using a 9 degree of freedom linear transformation. The subsequently fitted brain atlas provided an STN volume of 163 mm$^3$ that had a centroid located at X=−12.9, Y=−0.2, Z=−2.6 mm, relative to the patient's mid-commissural point. The post-operative CT was co-registered with the pre-operative MRI to determine the DBS lead location. The location of the four electrodes was then defined by placing a virtual 3389 DBS lead within the metal artifacts in the post-operative CT scan shown at 330-340 in FIG. 3.

Histological studies of the human STN have documented non-uniform neuronal densities as a function of location within the nucleus. These estimates suggest a neuronal density of ~1000 neurons/mm$^3$ in the dorsal STN and ~2000 neurons/mm$^3$ in the ventral STN. One study explicitly calculated neuronal densities from 9 different regions within the human STN (shown in Table 1, below), using post-mortem evaluations of 5 men with no known pathology. Based on this, the patient-specific STN volume of the example use case was voxelized to create 9 corresponding regions as shown at 350 in FIG. 3. A 3D point cloud was created for each region based on the specified neuronal densities shown in Table 1 below (in various other embodiments, neuronal densities of various sectors of the relevant brain region/nucleus can be similarly used in model creation). Each point in the STN volume represented a putative location for the cell body of a neuron model. The patient-specific model contained a total of 235,280 STN neurons (in various other embodiments, the number of neurons used in the model can vary based on estimates of the total number of neurons in the relevant brain region/nucleus for that embodiment). These neuron models within the STN volume provided the electrical sources for the LFP simulations, as discussed below in connection with FIG. 4. Every neuron was positioned with the longest axis of their dendritic field oriented along the rostro-caudal axis of the STN.

TABLE 1

| Neuronal Densities for each sector of the STN | |
| --- | --- |
| Anterior Dorsal | 1207 neurons/mm$^3$ |
| Anterior Central | 1148 neurons/mm$^3$ |
| Anterior Ventral | 1196 neurons/mm$^3$ |
| Middle Dorsal | 1431 neurons/mm$^3$ |
| Middle Central | 1472 neurons/mm$^3$ |
| Middle Ventral | 1611 neurons/mm$^3$ |
| Posterior Dorsal | 1269 neurons/mm$^3$ |
| Posterior Central | 1626 neurons/mm$^3$ |
| Posterior Ventral | 1872 neurons/mm$^3$ |

Figure 4:
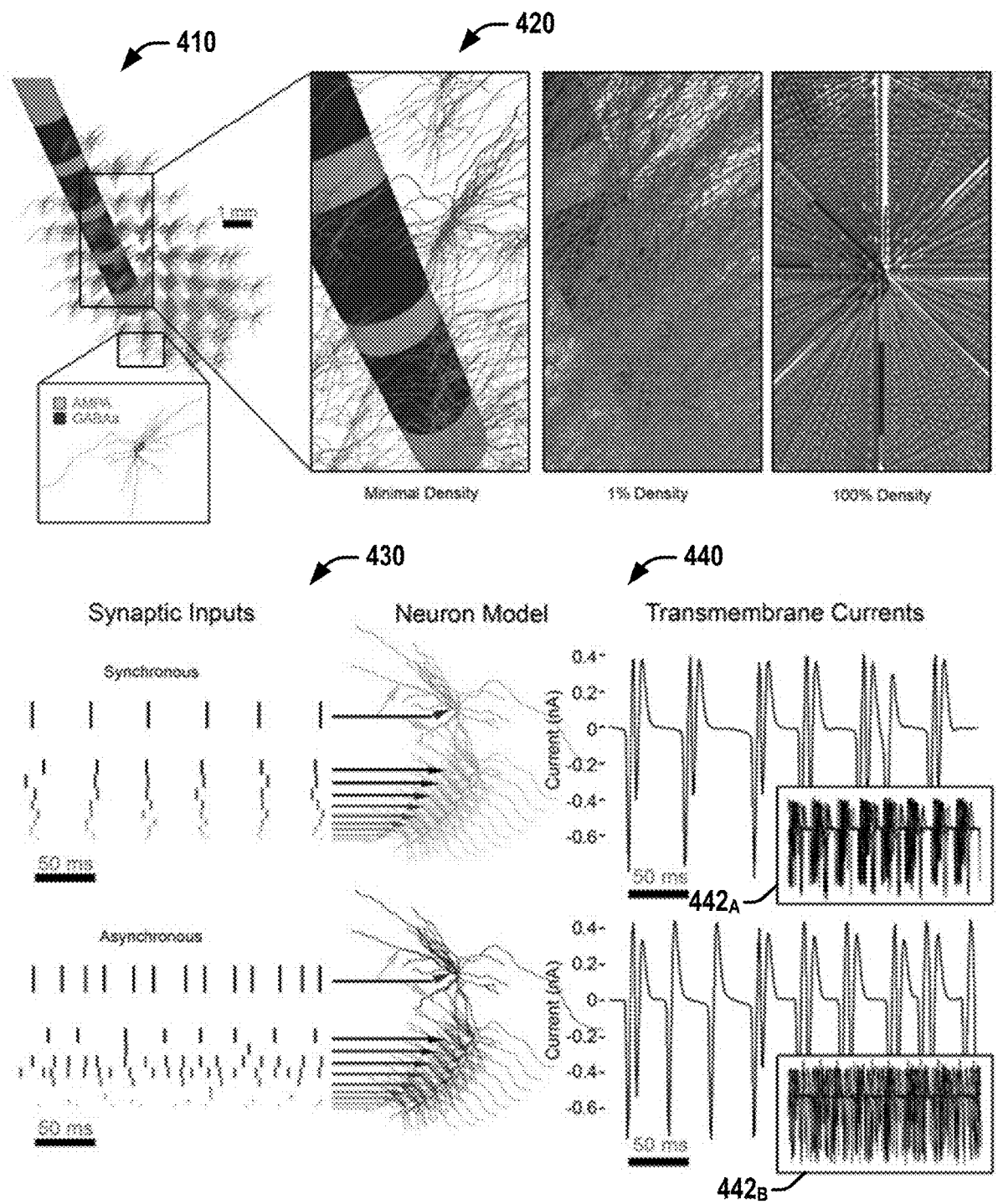
FIG. 4 illustrates a series of diagrams associated with neuron-source models according to various discussed herein.

Electrical Model:

Referring to FIG. 4, illustrated is a series of diagrams associated with neuron-source models according to various discussed herein. Diagram 410 shows the relative positioning of the DBS electrode (or other BS electrode in various embodiments) and STN (or other brain region/nucleus) neuron models with one neuron represented in each voxel of the STN volume. Each neuron received inhibitory (GABA$_A$) and excitatory (AMPA) synaptic input currents. Diagrams 420 shows a zoomed-in view of the full arborizations of the neuron models displayed at different densities (minimal, 1%, and 100%). At the full model density, spheres represent the soma locations. Diagrams 430 show example synaptic inputs (e.g., synchronous or asynchronous) and corresponding neuron models. In the model for the example use case, each of the 235,280 STN neuron models (e.g., as shown at diagrams 440) received a time varying oscillatory input pattern that triggered their synaptic currents. Inputs were either synchronous (the top row of diagrams 430 and 440) or asynchronous (the bottom rom of diagrams 430 and 440), with synchronous inputs designed to represent a 20 Hz beta pattern. Diagrams 440 show transmembrane current traces from the soma of a single neuron receiving synchronous (the top diagram of 440) or asynchronous (the bottom diagram of 440) synaptic inputs. The insets 442$_A$ and 442$_B$ in 440 show overlays of 10 different neurons demonstrating highly correlated output for the synchronous case, and no correlation for the asynchronous case.

The electrical source component of the overall LFP model system consisted of populations of multi-compartment cable models designed to represent STN projection neurons, as shown in FIG. 4. The neuron models were based on anatomical reconstructions of the STN neuron morphology and the electrical properties of STN neurons (for embodiments associated with other brain regions/nuclei, corresponding information can be employed for the relevant neuron models, which may vary from the STN-specific details discussed below based on the varying properties of neurons, neuron densities, etc. of different brain nuclei/regions. In such embodiments, corresponding data can be employed instead of the STN-specific information discussed below, but in a similar manner). Each STN neuron received 290 different synaptic inputs distributed over its structure for each synaptic input timing trigger, as discussed in greater detail below. Each somatic and dendritic compartment received either an excitatory or inhibitory synaptic input, with the inhibitory currents being slightly delayed. Dendritic compartments that were >100 μm from the soma were assigned glutamatergic (excitatory) inputs and the soma and dendritic compartments that were <100 μm were assigned GABAergic (inhibitory) inputs.

The synaptic inputs were represented as additional transmembrane currents in the neuron model ($I_{syn}=g_{syn}(V_m-E_{syn})$). The excitatory AMPA synapses were assigned a maximum conductance ($g_{max}$) of 0.5 nS and a reversal potential ($E_{rev}$) of 0 mV and the inhibitory GABA$_A$ synapses a $g_{max}$ of 0.5 nS and Erev of −80 mV. NEURON within the Python programming environment was employed to simulate all of the transmembrane currents generated by the neuron models.

Each STN neuron model was designated to receive either a synchronous beta pattern of synaptic inputs, or randomized un-correlated synaptic inputs, as shown at 430 and 440 in FIG. 4. For synchronous synaptic activity with a 20 Hz population mean, Gaussian noise with a standard deviation of 6.25 ms was added to the mean synaptic input times for each individual neuron. The onset times of synaptic inputs to the individual compartments of a particular neuron were also separated by randomly selecting from a normal distribution with a standard deviation of 16.25 ms about the mean synaptic input time for that individual neuron. These inputs represented synaptic activation times, which triggered the synaptic current associated with the given compartment to become active.

The asynchronous population of STN neurons was driven by randomized un-correlated synaptic inputs, as shown at lower diagrams of 430 and 440. The asynchronous inputs were constructed from an input frequency, $F_i$, randomly drawn from an exponential distribution. The exponential distribution had a mean of 20 Hz and was truncated to contain only values between 2 Hz and 200 Hz. These means were used to construct a time-domain input with a time constant of $1/F_i$, adding the same Gaussian noise as described above for the synchronous synaptic activity.

Neurons in the synchronous pool receiving the beta pattern of synaptic inputs exhibited highly correlated activity (e.g., as shown in the upper inset 442$_A$ of 440), while the neurons in the asynchronous pool receiving the randomized inputs exhibited uncorrelated activity (e.g., as shown in the lower inset 442$_B$ of 440). For the LFP simulations (discussed below), the net current flowing across the membrane of each compartment of each neuron was represented as an independent current source. The time-dependent transmembrane currents were calculated for a period of 1 second.

The volume conductor model consisted of a finite element model (FEM), which included a DBS electrode with the dimensions of the Medtronic 3389 DBS lead. The DBS electrode of the model was surrounded by a 0.1 mm interface layer that mimicked tissue encapsulation. The bulk brain tissue was assigned an isotropic conductivity of 0.2 S/m, typical of gray matter, and the interface layer was assigned an isotropic conductivity of 0.32 S/m. The FEM solution was generated in Comsol v5.1 (COMSOL, Burlington, Mass.).

Figure 5:
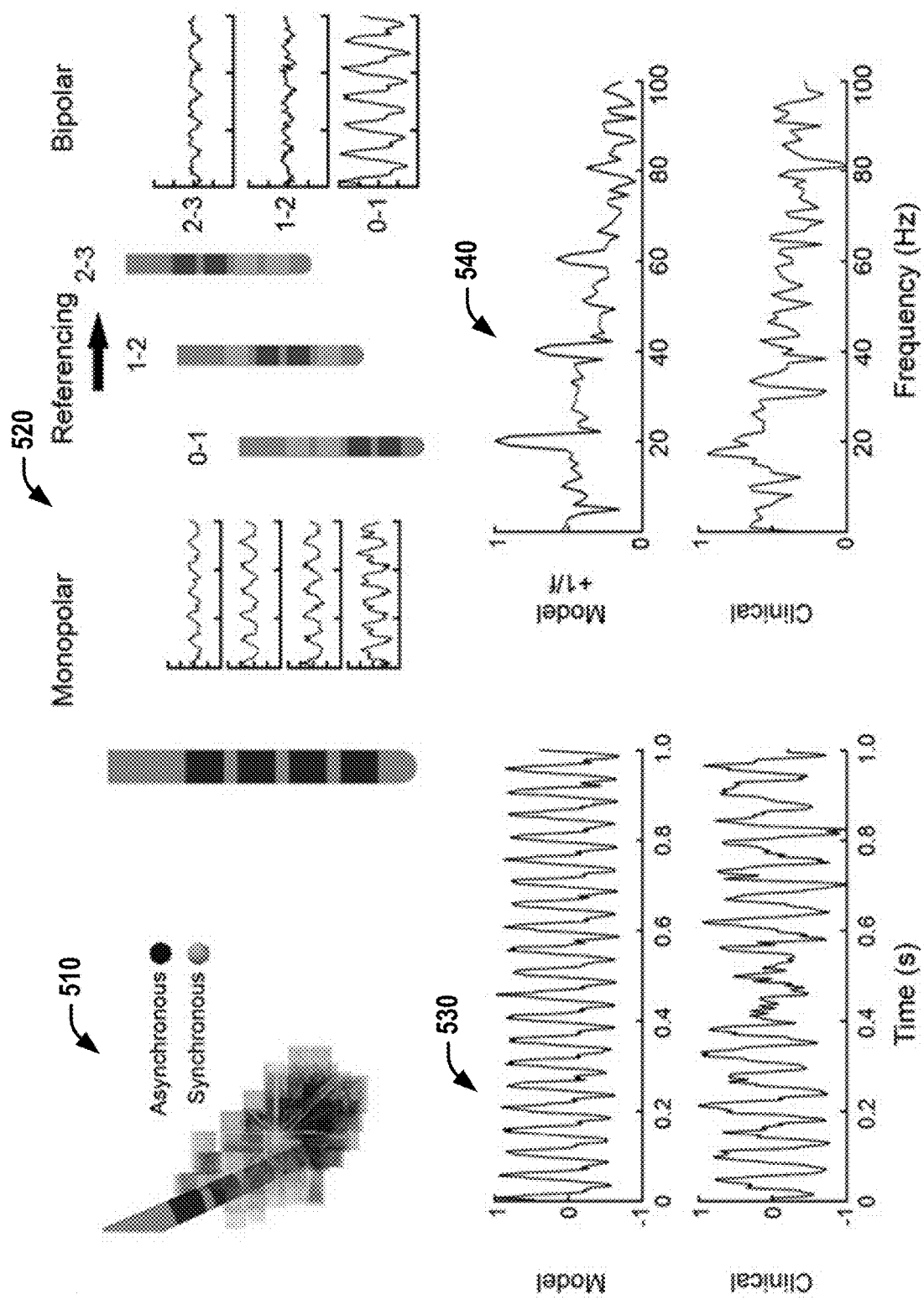
FIG. 5 illustrates a series of diagrams associated with an example integrated STN LFP (Local Field Potential) model, according to various aspects discussed herein.

Integrated STN LFP Model:

Referring to FIG. 5, illustrated is a series of diagrams associated with an example integrated STN LFP model, according to various aspects discussed herein. As shown at image 510, each STN neuron received either synchronous or asynchronous synaptic inputs. The model of the example use case used a radius of 3 mm, centered on contact 1, to define the synchronous neurons. In diagrams 520, the voltage recorded on each DBS electrode contact was defined from the sum of all transmembrane currents generated by each compartment of each neuron using a reciprocity based solution. Bipolar recording pairs were calculated as the difference between the appropriate monopolar recordings. Graphs 530 show a comparison of the time-domain simulated LFP to the clinical LFP recorded from the 0-1 contact pair. Normalized amplitudes are expressed in arbitrary units. Graphs 540 show power spectra of the model and clinical LFPs, showing beta activity in both cases. The example model of the example use case showed high amplitude narrow peaks not only at 20 Hz, but also at its harmonics (40, 60, and 80 Hz).

To simulate STN LFP recordings, the volume conductor model and electrical source models were coupled using a reciprocity-based solution, as shown in FIG. 5. In the coupled FEM-neuron population model, each compartment of each neuron was represented as an independent current source at the appropriate spatial location in the FEM. If any part of a STN neuron model intersected the DBS lead, that neuron was removed from the analysis. The recording voltage was calculated by summing the voltages generated at the electrode by the transmembrane currents of the individual neural compartments. This approach can be formulated mathematically as φ=K×I, where φ is a (1×t) vector containing the voltages recorded at t instances in time on the electrode, K is a (1×j) vector containing the voltages that would be impressed at the recording electrode for a unit current at the location of each of the j individual neuron compartments, and I is a (j×t) matrix containing the transmembrane currents for the individual neural compartments at each time step. The I matrix was calculated in NEURON, while each value in the K vector was derived from the FEM using a reciprocal solution.

The reciprocal solution involves placing a unit current source (i.e. 1 A) at the recording electrode and solving for the scalar potentials generated at each node in the FEM. By the theorem of reciprocity, the voltage at a given node in the FEM can be interpreted as the voltage that would be generated at the recording electrode for a unit current. Therefore, the contribution of each neural compartment to the recorded waveform (i.e., individual values in the K vector) can be calculated using interpolation of the voltages from the nearest nodes surrounding each neural compartment.

The $\phi$ for each DBS electrode contact represents the simulated monopolar LFP. The bipolar LFP was created by subtracting monopolar pairs with the same referencing scheme used for the clinical LFP recordings (for example, as shown in FIG. 5 at 520). To coincide with the clinical LFP recordings, the model LFPs were low-pass filtered at 100 Hz and down-sampled to 422 Hz. LFP analysis consisted of time domain amplitude measurements and power spectral density (PSD) measurements. Time domain amplitude was computed as the root-mean-square (RMS) amplitude of 1 second of the model LFP. PSDs were computed using Welch's method with a window size of 211, 50% overlap, and a fast Fourier transform length of 844. Beta power was defined as the mean of the PSD in the 15-22 Hz band. The model lacked a 1/f trend in its power spectra, a feature commonly observed in experimentally recorded LFPs. Therefore, a 1/f signal was added to all model LFPs for visual comparison purposes.

Normalized amplitudes were used to compare the model and clinical LFPs, which is also common practice in clinical LFP studies. This choice was also made because of uncertainty in the details of proprietary recording hardware and filtering circuitry of the Activa PC+S device. However, it should be noted that the model LFPs underestimated the Activa PC+S recording amplitudes by a factor of ~2.

Model Analysis:

The model of the example use case was employed to address three basic questions related to STN LFPs. First, what is the impact of the STN anatomy on the amplitude of the recorded signal? Second, what is the effect of moving a synchronous population of neurons within the STN? Third, what location and radius of synchronous STN neurons best matches the clinical recordings?

To explore the impact of incorporating a realistic STN anatomical volume into the LFP simulations the results generated from the patient-specific STN volume were compared to an idealized spherical STN volume (as discussed below in connection with FIG. 6). For the spherical STN, a uniformly spaced spherical grid was constructed that was volume matched to the patient-specific STN volume. Each node in the spherical grid was populated with a full multi-compartment STN neuron model, and the neurons received the same synaptic inputs as described for the patient-specific STN model. Contact 1 of the DBS electrode was then positioned at the geometric center of the spherical volume of STN neurons.

Figure 6:
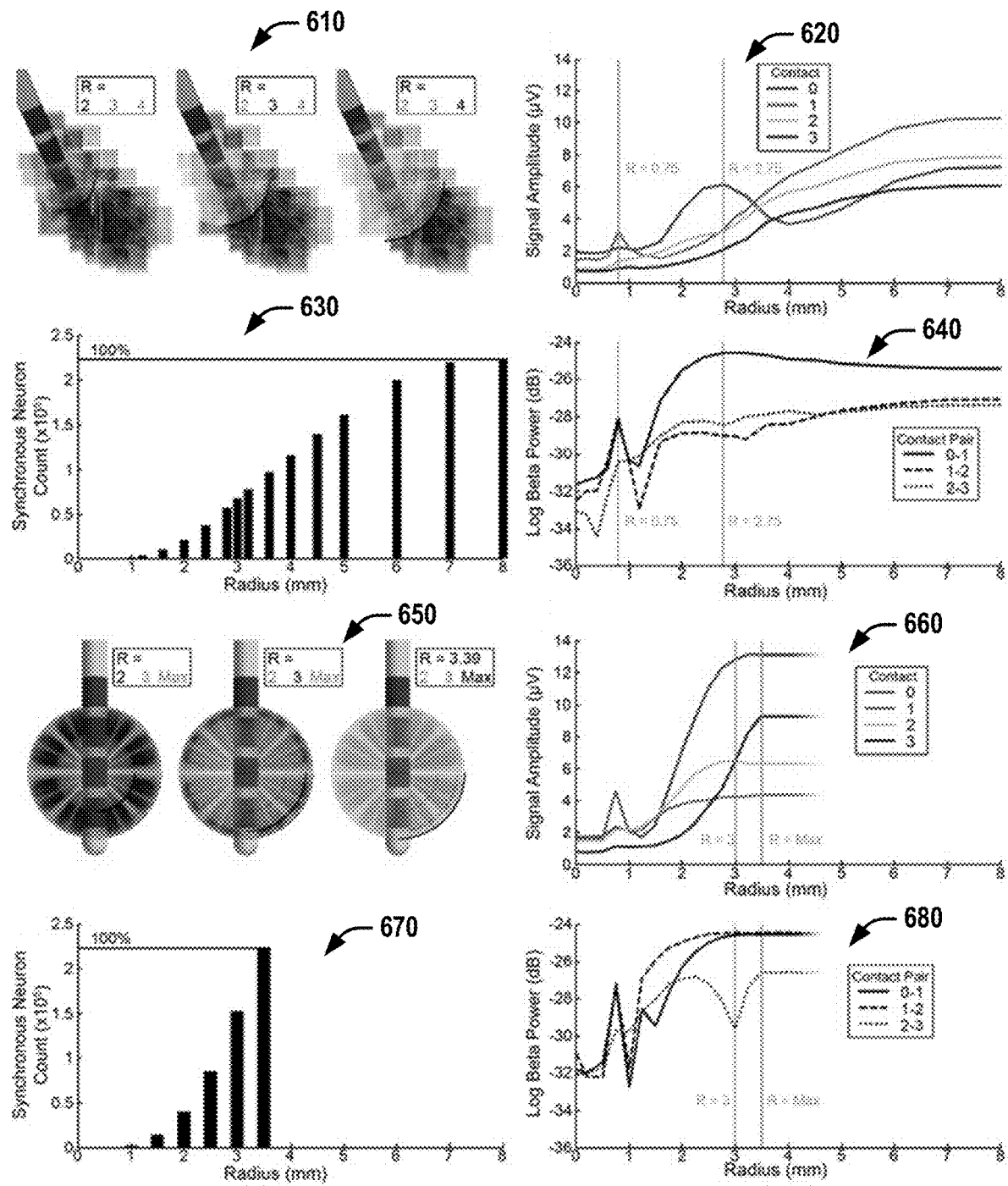
FIG. 6 illustrates a series of diagrams showing effects of the radius of synchronous STN neurons in a patient-specific STN LFP model compared with a spherical STN LFP model, according to various aspects discussed herein.

Referring to FIG. 6, illustrated is a series of diagrams showing effects of the radius of synchronous STN neurons in a patient-specific STN LFP model (610-640) compared with a spherical STN LFP model (650-680), according to various aspects discussed herein. Image 610 shows variations in the size of the synchronous neural population centered on contact 1 within the STN volume of the patient-specific STN LFP model. Graph 620 shows the RMS amplitude of the time domain LFP recorded on each monopolar contact of the patient-specific STN LFP model. Peaks at R=0.75 and R=2.75 reflect the envelope of the sphere of synchronous neurons passing the boundary of contact 1 and 0, respectively. Graph 630 shows the number of neurons in the patient-specific STN LFP model receiving synchronous input. Graph 640 shows the beta power of the LFP in the patient-specific STN LFP model for each of the bipolar contact pairs showing a maxima on contact pair 0-1 at R=2.75. Image 650 shows variations in the size of the synchronous neural population centered on contact 1 within a spherical volume for the spherical STN LFP model. The sphere has a volume matched to the patient-specific STN (163 mm$^3$). Graph 660 shows the RMS amplitude of the time domain LFP recorded on each monopolar contact for the spherical STN LFP model. Vertical lines represent R=3 where the amplitudes on contacts 2 and 3 are nearly identical and R=3.38, where the radius of the synchronous population equals that of the volume-matched sphere. As seen in graph 670, the number of synchronous neurons in the spherical STN LFP model increases with the cube of the radius until it fills the sphere. Graph 680 shows the beta power for each bipolar contact pair of the spherical STN LFP model. The case at R=3 where contacts 2 and 3 have nearly identical amplitude is represented as an abrupt drop, a consequence of the bipolar referencing scheme subtracting one from the other. In 610 and 650, the bolded number below R indicates the radius of synchronous activity.

To explore the effect of changing the radius of the synchronous activity, an arbitrary point was first defined as the center of the population of synchronous neurons. Then, STN model neurons whose cell bodies were within a radius R were designated as part of the synchronous population. The synaptic input times of these neurons were drawn from the pool of synchronous inputs. Synaptic inputs times for STN neurons that were outside of radius R were drawn from the asynchronous pool. The R for the patient-specific STN reconstruction varied from 0 mm (100% asynchronous) to 8 mm (100% synchronous) (as seen at 610). The R for the spherical comparator model varied from 0 mm (100% asynchronous) to 3.5 mm (100% synchronous) (as seen at 650).

To explore the effect of changing the location of the synchronous pool of neurons within the STN volume the long axis of the STN was defined and the pool was moved along that axis (as discussed in greater detail below in connection with FIG. 7). The long axis of the STN was defined by determining an anchor point within the volume that was farthest from the center of mass of the STN. The second anchor point was defined as the point farthest from the first point. These two points then formed a vector defining the long axis of the STN volume. The location of the center of the synchronous population of neurons was then centered on a point that moved along the long axis of the STN between the two extremes. Distances are expressed as a proportion of the long axis of the STN with a position of 0.0 corresponding to the ventral-medial aspect of the STN and a position of 1.0 corresponding to the dorsal-lateral end.

Model Optimization:

To compare the patient-specific model LFP to the clinical LFP, a fitness metric was developed that captured important features of the clinical LFP. For this optimization the shape of the power spectrum (implicitly including the relative magnitude of the peak in the beta band, without inclusion of the 1/f addition to the model) and the distribution of power in the beta band across the electrode array were considered. To capture these features, a fitness metric comprising two components was used. The first component was the Pearson's correlation coefficient between the model power spectra and the experimental power spectrum. The mean of the three coefficients, one for each comparison of the contact pairs, constituted 50% of the fitness metric. The remaining 50% of the fitness metric was computed using an asymmetry ratio. This asymmetry ratio compared the relative normalized narrow band beta power, and rewarded the model if a similar proportion of energy was in the beta band. The fitness metric can be expressed as shown in equation (1):

$$\frac{1}{6}\left(r_{01} + r_{12} + r_{23} + e^{-\ln\left(\frac{Bm_{01}}{Bc_{01}}\right)^2} + e^{-\ln\left(\frac{Bm_{12}}{Bc_{12}}\right)^2} + e^{-\ln\left(\frac{Bm_{23}}{Bc_{23}}\right)^2}\right) \quad (1)$$

where r is the Pearson's correlation coefficient between the normalized power spectra of the model LFP and the clinical LFP for each contact pair, and Bm and Bc are the normalized beta power in the model and clinical LFP, respectively. This fitness metric gave a value that varied between 0-1, and satisfies the condition that a relative beta-power twice as high as expected is penalized with equal severity as a beta power half as high as expected. Importantly, this metric captured similarity across all available contact pairs and utilized the full set of clinically-recorded LFPs to match the model LFPs.

Results

Simulations of STN LFPs for the example use case were designed to mimic the anatomical and electrical details of a tremor-dominant PD patient implanted with an Activa PC+S DBS system. The model consisted of 235,280 STN neurons positioned around a 3389 DBS electrode. To demonstrate the impact of the STN anatomy, the patient-specific simulations were compared to the results generated assuming an idealized sphere of STN neurons. To evaluate the role of neuronal synchrony, a population of STN neurons was driven with a beta pattern of synaptic inputs and modulated the location and radius of that synchronous population. It was found that explicitly representing the STN anatomy played an important role in the LFP recordings, and modulating the position and radius of neuronal synchrony substantially affected the amplitude and power of beta activity recorded by the DBS electrodes. Finally, clinical recordings were used to optimize the patient-specific LFP model and quantitatively estimate the position and radius of synchronous beta activity within the STN.

Radius of Synchrony:

One advantage of developing anatomically and electrically accurate models of STN LFPs (and similar models for other brain regions/nuclei) is the ability to address the basic biophysical question of how many neurons need to be synchronized to generate the clinical beta signal, which can facilitate more effective treatment of various conditions (e.g., tremor-dominant Parkinson's, etc.). The example use case (and similarly, other embodiments) initially considered driving a concentrated group of STN neurons with a highly synchronous beta pattern of activity (as in FIG. 5). Initially, the model was arbitrarily set up so that neurons within a radius of 3 mm of the center of contact 1 received synchronous input, while neurons outside that radius received asynchronous input. The monopolar representation of the LFP on each contact was converted into a bipolar LFP by subtracting each combination of contact pairs (as shown in FIG. 5 at 520). This initial patient-specific bipolar LFP model showed high beta activity in accordance with the clinically-recorded LFP from the same contact pair (as shown in FIG. 5 at 530). However, this initial model LFP contained harmonic peaks absent in the clinical LFP (as shown in FIG. 5 at 540).

To evaluate the role of the radius of synchronized activity on the LFP, the radius was incrementally increased from 0 and 8 mm, until every model STN neuron was receiving synchronous input (as discussed in connection with FIG. 6). The location of the center of the synchronous population remained fixed at the center of contact 1. Increasing the radius of synchronized neurons magnified the mean monopolar amplitude of the LFP in manner that was strongly correlated with the number of synchronous neurons (r=0.89, and as shown in FIG. 6 at 610-640), with exceptions at a radius of 0.75 and 2.75 mm. The time domain amplitude was highest on the most distal contact 0 for smaller populations, but fell off for greater radii. The remaining three contacts showed increasing time domain amplitudes, consistent with their distance from the synchronous neural population. Beta power measurements followed the same trend as time domain amplitude, with the same peaks at R=0.75 and 2.75 mm (as shown in FIG. 6 at 640).

The peaks at R=0.75 and 2.75 mm can be explained by a phase reversal of the effective dipole of the neurons. When the radius of synchronous neurons expanded past the distal borders of contacts 0 and 1, at R=0.75 and 2.75 mm, respectively, a phase reversal occurred. A neuron located at the superior aspect of a contact would have a contribution to the LFP equal and opposite to a neuron located inferior to the contact, assuming the geometry and orientation of the neurons remained constant. As the radius of synchronous neurons expanded beyond the border of the contact, more current sources were effectively canceled out by equal and opposite neurons in the distal part of the synchronous field. This effect was not observed for contacts 2 and 3, because contact 2 was partially outside the STN and contact 3 was located entirely outside of the STN.

The volume-matched spherical comparison LFP model also showed a correlation between the time domain amplitude and gross number of synchronous neurons (r=0.76, as shown in FIG. 6 at 650-680). As the radius of synchronous neurons increased contacts 0 and 2 exhibited the highest recording amplitudes, and contacts 0, 1, and 2 were affected by the phase reversal described above. The idealized sphere was more efficiently filled by the expanding radius of synchronous neurons, reaching maximum synchronicity at 3.38 mm.

Figure 7:
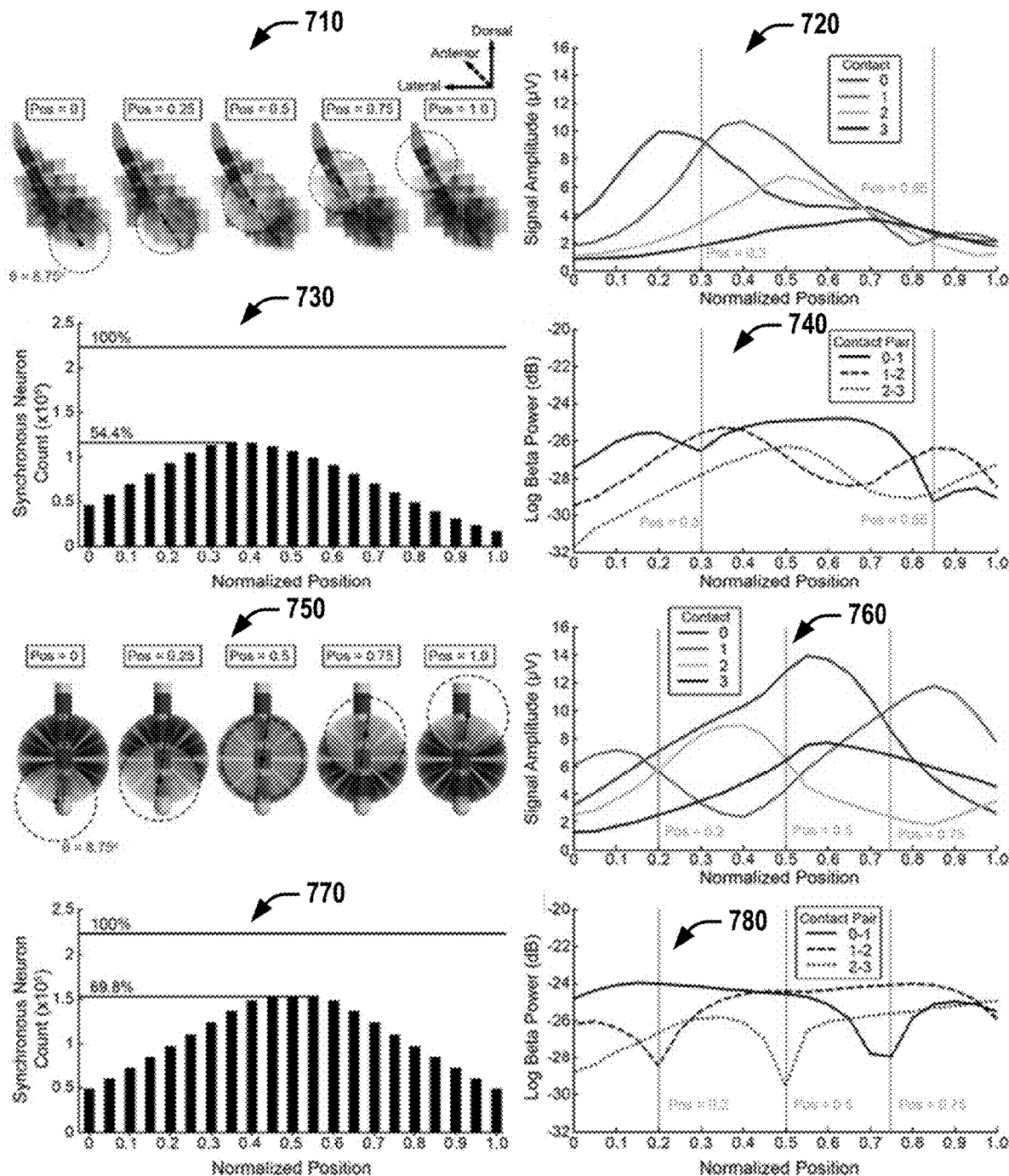
FIG. 7 illustrates a series of diagrams showing locations of synchronous STN neurons in a patient-specific STN LFP model compared with a spherical STN LFP model, according to various aspects discussed herein.

Location of Synchrony:

Referring to FIG. 7, illustrated is a series of diagrams showing locations of synchronous STN neurons in a patient-specific STN LFP model (710-740) compared with a spherical STN LFP model (750-780), according to various aspects discussed herein. Image 710 shows a 3 mm radius of synchronous neurons in different positions along the long-axis of the STN in the patient-specific STN LFP model. Graph 720 shows the RMS amplitude of the time domain model LFP on each of the monopolar contacts for the patient-specific STN LFP model. Graph 730 shows the number of STN neurons in the model receiving synchronous input as the synchronous population is moved in the patient-specific STN LFP model. Graph 740 shows the beta power of the model LFP for each bipolar contact pair showing minima on contact pairs that correspond to positions where the monopolar amplitudes are similar for the patient-specific STN LFP model. Image 750 shows a 3 mm radius of synchronous STN neurons in different positions within a spherical volume in the spherical STN LFP model. The trajectory of the synchronous population, relative to the DBS lead, had the same angle (8.75°) as the trajectory used in the patient-specific case. Graph 760 shows the RMS amplitude of the time domain spherical model LFP on each of the monopolar contacts for the spherical STN LFP model. Graph 770 shows the number of neurons in the spherical STN LFP model receiving synchronous input as the synchronous population is moved. Graph 780 shows the beta power for each bipolar contact pair in the idealized spherical STN LFP model. Vertical lines show local minima where the monopolar channels are similar in amplitude.

The position of the synchronous population was moved along the long axis of the STN. The position was expressed as a normalized quantity with 0.0 being the most ventral-medial aspect of the STN and 1.0 being the dorsal-lateral border (shown in FIG. 7 at 710-740). The long axis of the STN had a length of 10.2 mm, and the primary vector formed a compound angle of 8.75 degrees with the trajectory of the electrode. The radius of synchronization was fixed to 3.0 mm and moved from the ventral-medial border to the dorsal-lateral border of the STN. The mean monopolar amplitude was correlated with the gross number of synchronous neurons (r=0.58). The maximum number of synchronous neurons (128,020, or 54.4% of the total population) occurred at a position of 0.35.

The peak in the time domain amplitude recorded at each contact occurred when the average distance from the center of the contact to the center of the synchronous population was 1.9 mm (shown in FIG. 7 at 720). The time domain amplitudes were lower in the dorsal-lateral STN due to the geometry of the nucleus boundary and the lower neural density, which resulted in fewer synchronous neurons (shown in FIG. 7 at 730). Beta power as a function of the position of the synchronous neurons tracked the time domain amplitude of the respective contacts used in the bipolar recording (shown in FIG. 7 at 740).

The volume-matched spherical LFP model had a maximum number of synchronous neurons (164,225) at the position of 0.5 (shown in FIG. 7 at 770). The time domain amplitudes exhibited a phase reversal when the center of the contact was close to the center of the synchronous population (shown in FIG. 7 at 760). For example, the local minima for the contact 1 monopolar amplitude coincided with a position of 0.4. The beta power then followed the synchronous population as it traversed the volume of neurons (shown in FIG. 7 at 780).

Figure 8:
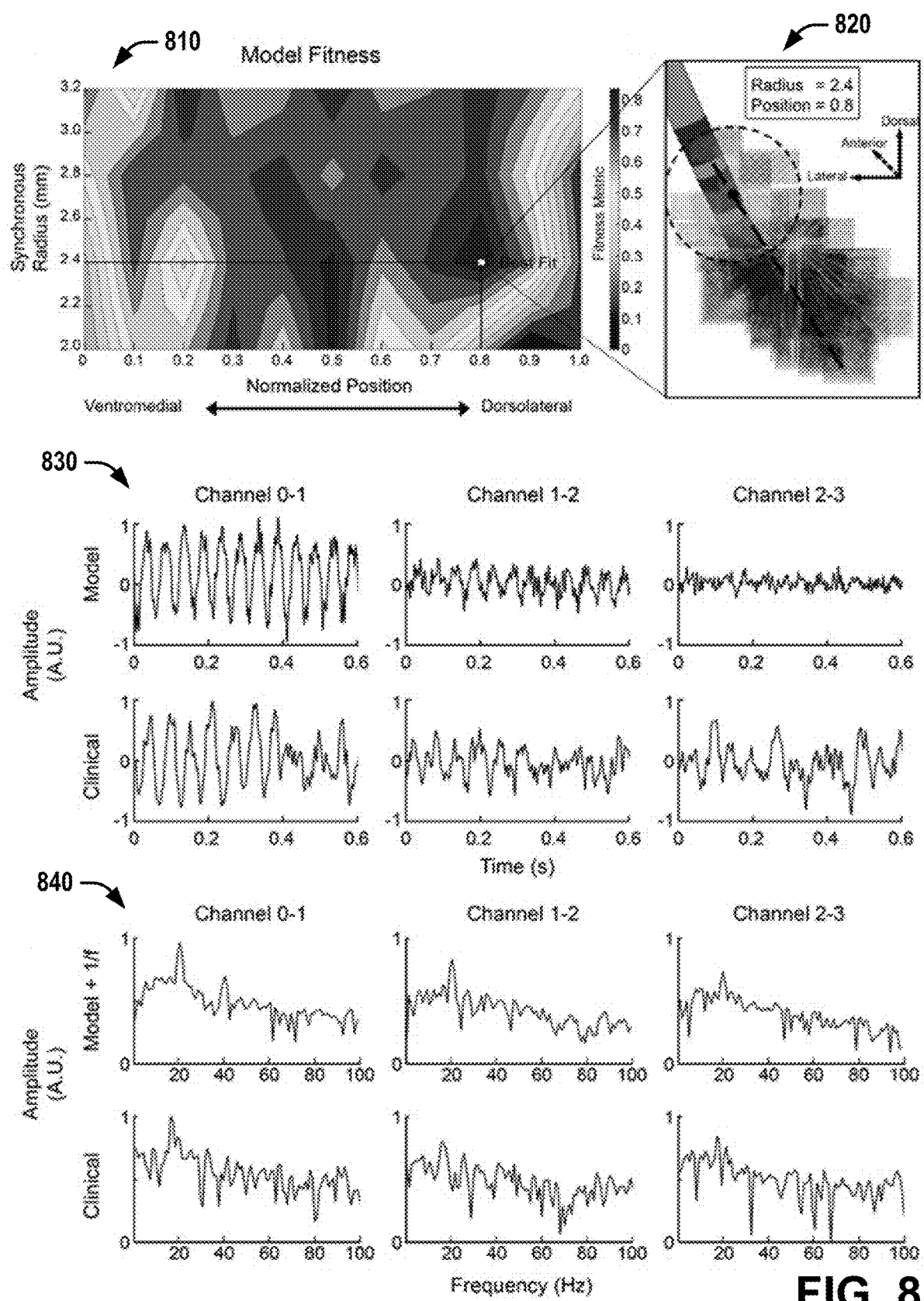
FIG. 8 illustrates a series of diagrams showing an example of an optimized STN LFP model, according to various aspects discussed herein.

Model Optimization:

Referring to FIG. 8, illustrated is a series of diagrams showing an example of an optimized STN LFP model, according to various aspects discussed herein. Image 810 shows a search of the parameter space to find an optimal synchronous radius and normalized position. The fitness metric incorporated coherence between the clinical and model power spectra, as well as the relative normalized beta power across the contact pairs. Image 820 shows a visual schematic of the optimized STN LFP model, indicating optimal radius and position values for the example use case. The positions of synchronized and unsynchronized neurons are shown in light gray and dark gray, respectively. Graphs 830 show comparisons of the time domain results for the model and clinical LFPs for various contact pairs. In both cases, the highest amplitude signals were recorded across contact pair 0-1. Graphs 840 show comparisons of the model and experimental power spectra. Both cases show high beta power for the contact pair 0-1. The optimized model shows much lower amplitude harmonics relative to the non-optimized patient-specific model used in FIG. 5.

The patient-specific LFP model was used to estimate the location and radius of synchronous beta activity within the STN using clinically-recorded LFPs from each of the 3 bipolar pairs, as shown in FIG. 8. The model was swept through 77 parameter pairs of radius (ranging from 2.0-3.2 mm) and normalized position (ranging from 0.0-1.0) of synchronized activity in the STN. Model fitness was assessed using equation 1, as shown in FIG. 8 at 810. Parameter sets with low amplitude and extreme positions (close to 1 or 0) showed low model fitness, as very few neurons were receiving synchronous input in those cases. Parameters sets with a larger radius and more central positions showed high beta power; however, they poorly matched with the clinical recordings with respect to the distribution of beta power across the electrode array. One exception was an island of high fitness with a radius of −2 mm and a position of 0.5. These model parameters corresponded to the synchronous volume approximately centered on contact 1. However, the peak model fitness was achieved at radius of 2.4 mm and position of 0.8, which corresponded to the synchronous volume approximately centered on contact 2, as shown in FIG. 8 at 810-820. These optimized parameters consisted of 36,580 neurons localized in the dorsolateral aspect of the STN. The optimized model showed a high recording amplitude on contact pair 0-1, and lower amplitudes on the other pairs, similar to the clinical data, as shown in FIG. 8 at 830. Additionally, the model power spectra compared favorably to the clinical power spectra, as shown in FIG. 8 at 840. When compared with the initial (non-optimized) STN LFP model parameters of FIG. 5, harmonics were noticeably reduced on the 0-1 contact pair, and absent on other contact pairs.

Scientific analyses of LFP data acquired from DBS electrodes have expanded rapidly over the last decade and these results are beginning to drive novel advances in the clinical application of DBS technology. However, detailed biophysical understanding of the anatomical and electrical variables that dictate the clinically recorded LFP signals has been limited. The example use case provides the first quantitative estimates of the spatial extent of the recording volume and the number of neurons responsible for the beta activity commonly observed in the human STN. The model employs patient anatomy and neural synchrony in defining the magnitude and power of the recorded signal. The example use case and results obtained therefrom were derived from first principles, with explicit representation of the synaptic input currents, neuronal spiking activity, and volume conducted electric fields, all integrated within an anatomically realistic context, as shown in FIGS. 3-4.

As shown via the example use case, monopolar recordings followed relatively simple and expected relationships; however, the patient-specific LFP model results highlight the complexities of understanding and interpreting bipolar recordings from clinical DBS electrodes, as shown via FIGS. 6-7. Given that bipolar recordings are the preferred (or often required) method of clinical data collection, the model of the example use case provides some important insight that should be considered when using LFP signals to estimate the localization of neuronal synchrony, as shown via FIG. 8. For example, the center of neural synchrony is not typically centered between the contact pair that has the greatest signal. As such, in the example use case (and in other various embodiments) all of the available recording pairs can be used together to determine which of the individual contacts is actually positioned most closely to the center of neural synchrony, as shown in FIGS. 7-8. Additionally, while the optimized model of the example use case predicted that the center of neural synchrony in the example patient was closest to contact 2, it was actually stimulation through contact 1 that provided the greatest therapeutic benefit. While the example use case was based on only one patient, this result reinforces the concept that many different factors dictate the optimal contact for stimulation, and LFP-based identification of a contact associated with high neural synchrony may only be one piece of the clinical puzzle.

One key benefit of DBS LFPs is the opportunity to simultaneously record from multiple contacts and then use that information to help localize the source. The conclusion that a synchronous dorsolateral region best fit the experimental recordings of the example use case was not necessarily because of proximity of the synchronous population to a given contact (e.g., in FIG. 8 at 810, position 0.2 was very close to contact 0). Instead, the optimized model was defined using the combined signals observed on all of the contact pairs. This highlights the point that coupled integration of as many independent pieces of data as possible (e.g. imaging, anatomy, and electrophysiology), as in various embodiments discussed herein, can help to constrain the number of realistic solutions that are possible for the "inverse problem" of source localization that theoretically has an infinite number of solutions.

The substantial growth in clinical STN LFP data collection for scientific analyses has provided the foundation for wide-ranging correlative associations between beta-band activity and Parkinsonian symptoms. Pragmatic translation of these scientific findings can provide advances to the clinical practice of DBS in the form of advanced intraoperative targeting algorithms, and electrode contact selection methods for therapeutic stimulation. In addition, the chronic recording of STN LFP beta can also be used as an electrophysiological biomarker in adaptive DBS control systems. Various embodiments discussed herein can facilitate more sophisticated LFP-based clinical algorithms, by providing more detailed and quantitative understanding of the underlying biophysical factors dictating the recorded signals. Unfortunately, interpretation of LFPs can be influenced by many different factors. Therefore, various embodiments discussed herein incorporate and account for variables that are likely to play the biggest role in creating patient-to-patient variability in STN LFP recordings (or LFP recordings from other brain regions/nuclei, in various embodiments). These variables include the anatomy of the patient, the position of the electrode, and the location/size of neural synchrony. Results from the example use case show that all of these factors are important in shaping the LFP and that the patient-specific modeling approach employed by various embodiments discussed herein can be used to account for these sources of variability, for example, as can be seen in connection with FIGS. 6-7.

The LFP models created for the example use case are complicated and technically demanding to implement. As such, various embodiments employed for large-scale clinical research studies or integration into LFP-based clinical algorithms can be simplified in one or more ways relative to the model of the example use case. However, the models created for the example use case represent a theoretical "gold standard" that can be used to develop and evaluate simplified, but still patient-specific, LFP models that are capable of capturing the salient features of the detailed model system, while also being computationally tractable for larger-scale analyses (e.g., embodiments employing point neurons instead of multi-compartment neurons, etc.). Such simplified models could become especially useful as clinical DBS systems greatly expand the number of electrode contacts available for both stimulation and recording. This added electrode complexity provides more flexibility for therapeutic optimization, but will likely also require algorithmic tools to help process and interpret the LFP data to enable identification of the optimal DBS control system for the patient. For example, if the underlying goal of a closed-loop DBS algorithm is to efficiently stimulate the neurons that are responsible for creating the beta oscillation, then the amplitude of the beta oscillation recorded at each contact provides only part of the information needed to customize the therapy to the patient. By calculating a center and radius of the synchronous population, a patient-specific LFP model can provide a "target volume" which can be used not only in defining an optimal recording configuration for chronic monitoring, but also in stimulation contact selection and the tuning of stimulation amplitudes to optimize modulation of that target. Various embodiments can facilitate determination of a target volume for monitoring and/or modulation via DBS (or other BS, in various embodiments) electrode stimulation, via determination of at least one contact stimulation, stimulation amplitude, etc.

While the patient-specific STN LFP model of the example use case is highly detailed, the accuracy can potentially be improved in various respects, with a tradeoff in efficiency (as noted above, given current computing capabilities, lesser accuracy and greater efficiency can also be employed for more widespread clinical application). One limitation of the example use case was the accuracy in which the location of the electrode was defined within the anatomy. The relative location of the electrode to the STN could be off by ~1 mm in any direction. Thus, in various embodiments, electrode locations can be determined with a higher degree of accuracy, which can, for such embodiments, better correlate patient-specific electrode locations with anatomical regions of high neural synchrony.

One discrepancy between the example use case and the PC+S recordings was the model underestimating the raw signal amplitudes by a factor of ~2 (however, when normalized, the model was closely aligned). If one takes the PC+S recordings as a "gold standard", two physiological features may be able to reconcile this model limitation. First, human STN neurons are likely larger than the macaque STN neuron models used in the simulations. A scaling factor of 3 would be consistent with general brain size and nucleus size differences, which would coincide with a larger magnitude of synaptic currents and membrane currents per neuron; thus, various embodiments can employ such a scaling factor (e.g., 3, or some other value for a scaling factor). Second, not all beta signals recorded by subthalamic DBS electrodes come from the STN. Volume conducted currents from other brain regions (e.g., cortex) likely play a measureable role, and the model ignores these external currents.

Additionally, as noted above, the model does not comprise an intrinsic 1/f distribution in the power spectrum, which is a common deficiency in LFP models typically attributed to ionic diffusion. In addition, the absence of a 1/f pattern in the model was also likely due to the homogeneity of the frequency of synaptic inputs. In some embodiments, the constant frequency can be replaced with inputs drawn from an exponential distribution can result in a 1/f pattern; however, this comes at the expense of overall model synchrony (which further exacerbates the recording amplitude limitation of the model).

An additional simplifying assumption that was employed in the example use case (but that can be varied in some embodiments) was the decision to represent regions of synchrony as a sphere. Representing the region of synchrony as a sphere can be useful for interpreting clinical LFP signals. However, the model infrastructure and associated techniques discussed herein allow for the use of any synaptic input pattern to any of the neurons and can also be employed for analysis of more complicated forms of synchrony. Various embodiments employing more complicated forms of synchrony can be guided by specific anatomical connectivity patterns (e.g., hyperdirect vs. pallidal inputs) and precise electrophysiological hypotheses (e.g., high frequency (~300 Hz) vs. low frequency (~20 Hz) oscillations).

ADDITIONAL EMBODIMENTS

As demonstrated by the example embodiments, various embodiments can facilitate identification of a target area (and/or optimal BS electrode(s) and/or stimulation amplitude(s)) within a brain region that can facilitate monitoring and/or stimulation of the brain region via one or more implanted BS electrodes for monitoring and/or treatment of an associated medical condition.

In various example embodiments, method(s) discussed herein can be implemented as computer executable instructions. Thus, in various embodiments, a computer-readable storage device can store computer executable instructions that, when executed by a machine (e.g., computer, processor), cause the machine to perform methods or operations described or claimed herein including operation(s) described in connection with methods 100, 200, or any other methods or operations described herein. While executable instructions associated with the listed methods are described as being stored on a computer-readable storage device, it is to be appreciated that executable instructions associated with other example methods or operations described or claimed herein can also be stored on a computer-readable storage device. In different embodiments, the example methods or operations described herein can be triggered in different ways. In one embodiment, a method or operation can be triggered manually by a user. In another example, a method or operation can be triggered automatically.

Embodiments discussed herein related to identification of target areas (and/or optimal BS electrode(s) and/or stimulation amplitude(s)) for monitoring or stimulation via implanted BS electrodes involve computer-based models derived from radiographic images and features not perceivable by the human eye, computations that cannot be practically performed in the human mind, and involve specific neuroanatomy in connection with the position and orientation of BS electrodes implanted within or near that neuroanatomy. Computer models as described herein cannot be implemented in the human mind or with pencil and paper. Embodiments thus perform actions, steps, processes, or other actions that are not practically performed in the human mind, at least because they require a processor or circuitry to access digitized images stored in a computer memory and to extract or compute features that are based on the digitized images and not on properties of tissue or the images that are perceivable by the human eye. Embodiments described herein can use a combined order of specific rules, elements, operations, or components that render information into a specific format that can then be used and applied to create desired results more accurately, more consistently, and with greater reliability than existing approaches, thereby producing the technical effect of improving the performance of the machine, computer, or system with which embodiments are implemented.

Figure 9:
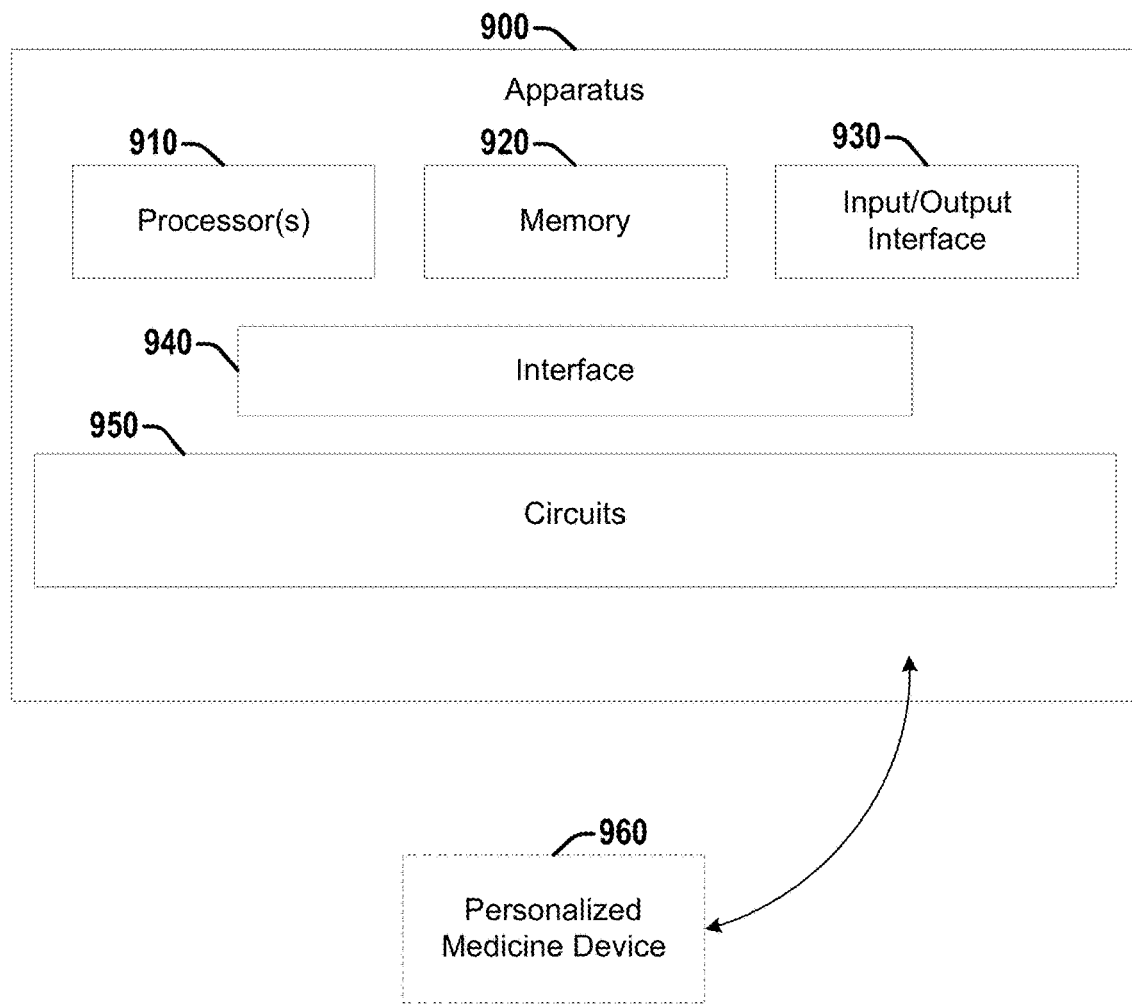
FIG. 9 illustrates a diagram of a first example apparatus 900 that can facilitate identification of a target area (and/or optimal BS electrode(s) and/or stimulation amplitude(s)) for monitoring or stimulation via implanted BS electrodes, according to various embodiments discussed herein.

Referring to FIG. 9, illustrated is a diagram of a first example apparatus 900 that can facilitate identification of a target area (and/or optimal BS electrode(s) and/or stimulation amplitude(s)) for monitoring or stimulation via implanted BS electrodes, according to various embodiments discussed herein. Apparatus 900 can be configured to perform various techniques discussed herein, for example, various operations discussed in connection with sets of operations 100 and/or 200. Apparatus 900 comprises one or more processors 910. Apparatus 900 also comprises a memory 920. Processor(s) 910 can, in various embodiments, comprise circuitry such as, but not limited to, one or more single-core or multi-core processors. Processor(s) 910 can include any combination of general-purpose processors and dedicated processors (e.g., graphics processors, application processors, etc.). The processor(s) can be coupled with and/or can comprise memory (e.g., of memory 920) or storage and can be configured to execute instructions stored in the memory 920 or storage to enable various apparatus, applications, or operating systems to perform operations and/or methods discussed herein. Memory 920 can be configured to store one or more radiological images of a brain region (e.g., CT, MRI, etc.), for example, whole brain imaging, or imaging comprising a subset of the whole brain that comprises the relevant brain region and BS electrodes. Each of the radiological image(s) can have a plurality of pixels, each pixel having an associated intensity; 3D imaging data can have a plurality of voxels, each voxel having an associated intensity. Memory 920 can be further configured to store additional data involved in performing operations discussed herein, such as for models employed to identify a target area (and/or optimal BS electrode(s) and/or stimulation amplitude(s)) for monitoring or stimulation via implanted BS electrodes.

Apparatus 900 also comprises an input/output (I/O) interface 930 (e.g., associated with one or more I/O devices), a set of circuits 950, and an interface 940 that connects the processor 910, the memory 920, the I/O interface 930, and the set of circuits 950. I/O interface 930 can be configured to transfer data between memory 920, processor 910, circuits 950, and external devices, for example, a medical imaging device (e.g., MRI system or apparatus, CT system or apparatus, etc.), a BS system or apparatus for controlling the implanted BS electrodes, and/or one or more remote devices for receiving inputs and/or providing outputs to a clinician, patient, etc., such as optional personalized medicine device 960.

The processor(s) 910 and/or one or more circuits of the set of circuits 950 can be configured to receive one or more radiological images (e.g., from memory 920 or from an external device, etc.). The one or more radiological images can comprise pre-operative imaging and post-operative imaging, which can provide detailed information regarding patient-specific neuroanatomy, as well as position and orientation of the BS electrodes.

The processor(s) 910 and/or one or more circuits of the set of circuits 950 can be further configured to generate a patient-specific anatomical model based on radiological imaging and known neuroanatomical information of the region and/or sub-regions of the brain region.

The processor(s) 910 and/or one or more circuits of the set of circuits 950 can be further configured to populate the patient-specific anatomical model with individual neuron models based on the neuronal densities of the brain region and the sub-regions, to model the operation of a number of neurons approximately equal to the actual number of neurons in the brain region. Properties of the populated neuronal models can be based on measured properties of neurons from the brain region and/or each sub-region (e.g., number of synaptic inputs, etc.). Additionally, depending on the embodiment, the type of neuron models employed can vary, and can be, for example, relatively simple models (which can provide improved computation efficiency) such as point neurons, or can be more complicated neuron models (e.g., multi-compartment neurons as discussed in the example use case, etc.), which can provide improved model accuracy.

The processor(s) 910 and/or one or more circuits of the set of circuits 950 can be further configured to construct a patient-specific LFP (local field potential) model of the brain region based on the populated patient-specific anatomical model. The LFP model can comprise an electrical source model comprising the populated neuron models at their associated locations (e.g., evenly distributed through the brain region and/or each sub-region based on the associated densities, etc.) and a volume conductor model that can model conduction through the brain region and/or each sub-region, as well as in the vicinity of the BS electrodes.

The processor(s) 910 and/or one or more circuits of the set of circuits 950 can be further configured to determine a reciprocal solution from the patient-specific LFP model of the brain region, based on determining the voltage at locations of neurons (e.g., finite element model (FEM) nodes) in the patient-specific LFP model based on a test unit current source, to calculate contributions to a waveform from individual neuron models of the patient-specific LFP model.

The processor(s) 910 and/or one or more circuits of the set of circuits 950 can be further configured to identify, based on the reciprocal solution, a target area in the brain region (and/or optimal BS electrode(s) and/or stimulation amplitude(s)) for monitoring and/or stimulation via at least one of the BS electrodes. In various embodiments, identifying the target area can comprise identifying a size, location, and/or shape of the target area, although in various embodiments the shape can be approximated with a simpler model (e.g., spherical) to improve efficiency while still providing clinically useful results.

Apparatus 900 can optionally further comprise personalized medicine device 960. Apparatus 900 can be configured to provide the prognosis, personalized treatment plan, or other data to personalized medicine device 960. Personalized medicine device 960 may be, for example, a computer assisted diagnosis (CADx) system or other type of personalized medicine device that can be used to facilitate monitoring and/or treatment of an associated medical condition. In some embodiments, processor(s) 910 and/or one or more circuits of the set of circuits 950 can be further configured to control personalized medicine device 960 to display the identified target area, optimal BS electrode(s), recommended stimulation amplitude(s), or other data on a computer monitor, a smartphone display, a tablet display, or other displays.

Examples herein can include subject matter such as an apparatus, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for identifying a target area within a brain region for monitoring and/or stimulation via BS electrode lead(s), according to embodiments and examples described.

Example 1 is a non-transitory computer-readable medium storing computer-executable instructions that, when executed, cause a processor to perform operations, comprising: generating, based on radiological imaging of a region of a brain of a patient and one or more Brain Stimulation (BS) electrode leads implanted in or near the region, a patient-specific anatomical model of the region and the one or more BS electrode leads; populating the patient-specific anatomical model with a plurality of neuron models based on at least one associated neuronal densities of at least one of the region or one or more sub-regions of the region; constructing a patient-specific local field potential (LFP) model of the region based on the patient-specific anatomical model and an associated location and associated orientation for each BS electrode lead of the one or more BS electrode leads; determining a reciprocal solution from the patient-specific LFP model; and identifying, based on the reciprocal solution, a target area within the region for at least one of monitoring or treatment of a medical condition via the one or more BS electrode leads.

Example 2 comprises the subject matter of any variation of any of example(s) 1, wherein the operations further comprise identifying, via the patient-specific LFP model of the region, at least one BS electrode lead of the one or more BS electrode leads that maximizes stimulation of the target region within a selected frequency range.

Example 3 comprises the subject matter of any variation of any of example(s) 2, wherein the operations further comprise determining, via the patient-specific LFP model of the region, at least one optimal stimulation amplitude for stimulating the target region via the at least one BS electrode lead for treatment of the medical condition.

Example 4 comprises the subject matter of any variation of any of example(s) 1-3, wherein identifying, via the patient-specific LFP model of the region, the target area comprises determining a size and a position of the target area.

Example 5 comprises the subject matter of any variation of any of example(s) 4, wherein the size and the position of the target area are determined based on a fitness metric.

Example 6 comprises the subject matter of any variation of any of example(s) 4-5, wherein the target area comprises a spherical region, the size is a radius of the spherical region, and the position is a center of the spherical region.

Example 7 comprises the subject matter of any variation of any of example(s) 1-6, wherein the radiological imaging comprises a pre-operative MRI (Magnetic Resonance Imaging) image of the region prior to implantation of the one or more BS electrode leads and a post-operative CT (Computed Tomography) image of the region and the one or more BS electrode leads.

Example 8 comprises the subject matter of any variation of any of example(s) 1-7, wherein each neuron model of the plurality of neuron models is a point neuron model.

Example 9 comprises the subject matter of any variation of any of example(s) 1-7, wherein each neuron model of the plurality of neuron models is a multi-compartment neuron model.

Example 10 comprises the subject matter of any variation of any of example(s) 1-9, wherein the instructions further comprise determining contributions to a waveform of individual neuron models of the plurality of neuron models from the reciprocal solution.

Example 11 is an apparatus that facilitates identification of a target area of a region of a brain for treatment of a medical condition, the apparatus comprising: a memory configured to store radiological imaging of a region of a brain of a patient and one or more Brain Stimulation (BS) electrode leads implanted in or near the region; and one or more processors configured to: generate, based on the radiological imaging of the region of the brain of the patient and the one or more Brain Stimulation (BS) electrode leads implanted in or near the region, a patient-specific anatomical model of the region and the one or more BS electrode leads; populate the patient-specific anatomical model with a plurality of neuron models based on at least one associated neuronal densities of at least one of the region or one or more sub-regions of the region; construct a patient-specific local field potential (LFP) model of the region based on the patient-specific anatomical model and an associated location and associated orientation for each BS electrode lead of the one or more BS electrode leads; determine a reciprocal solution from the patient-specific LFP model; and identify, based on the reciprocal solution, a target area within the region for at least one of monitoring or treatment of a medical condition via the one or more BS electrode leads.

Example 12 comprises the subject matter of any variation of any of example(s) 11, wherein the one or more processors are further configured to identify, via the patient-specific LFP model of the region, at least one BS electrode lead of the one or more BS electrode leads that maximizes stimulation of the target region within a selected frequency range.

Example 13 comprises the subject matter of any variation of any of example(s) 12, wherein the one or more processors are further configured to determine, via the patient-specific LFP model of the region, at least one optimal stimulation amplitude for stimulating the target region via the at least one BS electrode lead for treatment of the medical condition.

Example 14 comprises the subject matter of any variation of any of example(s) 11-13, wherein the one or more processors are configured to identify, via the patient-specific LFP model of the region, the target area comprises determining a size and a position of the target area.

Example 15 comprises the subject matter of any variation of any of example(s) 14, wherein the size and the position of the target area are determined based on a fitness metric.

Example 16 comprises the subject matter of any variation of any of example(s) 14-'5, wherein the target area comprises a spherical region, the size is a radius of the spherical region, and the position is a center of the spherical region.

Example 17 comprises the subject matter of any variation of any of example(s) 11-16, wherein the radiological imaging comprises a pre-operative MRI (Magnetic Resonance Imaging) image of the region prior to implantation of the one or more BS electrode leads and a post-operative CT (Computed Tomography) image of the region and the one or more BS electrode leads.

Example 18 comprises the subject matter of any variation of any of example(s) 11-17, wherein each neuron model of the plurality of neuron models is a point neuron model.

Example 19 is a non-transitory computer-readable medium storing computer-executable instructions that, when executed, cause a processor to perform operations, comprising: generating, based on radiological imaging of a region of a brain of a patient and one or more Brain Stimulation (BS) electrode leads implanted in or near the region, a patient-specific anatomical model of the region and the one or more BS electrode leads; voxelizing the patient-specific anatomical model to create a plurality of model sub-regions corresponding to a plurality of sub-regions of the region of the brain; populating the plurality of model sub-regions with associated pluralities of neuron models based on associated neuronal densities of the corresponding plurality of sub-regions of the brain; constructing a patient-specific local field potential (LFP) model of the region based on the patient-specific anatomical model and an associated location and associated orientation for each BS electrode lead of the one or more BS electrode leads; determining a reciprocal solution from the patient-specific LFP model; and identifying, via the reciprocal solution determined from the patient-specific LFP model of the region, a size and a location of a target area within the region for at least one of monitoring or treatment of a medical condition via the one or more BS electrode leads.

Example 20 comprises the subject matter of any variation of any of example(s) 19, wherein the operations further comprise identifying, via the patient-specific LFP model of the region, at least one BS electrode lead of the one or more BS electrode leads that maximizes stimulation of the target region within a selected frequency range.

Example 21 comprises an apparatus comprising means for executing any of the described operations of examples 1-20.

Example 22 comprises a machine readable medium that stores instructions for execution by a processor to perform any of the described operations of examples 1-20.

Example 23 comprises an apparatus comprising: a memory; and one or more processors configured to: perform any of the described operations of examples 1-20.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable medium storing computer-executable instructions that, when executed, cause a processor to perform operations, comprising:
   generating, using radiological imaging of a region of a brain of a patient and Brain Stimulation (BS) electrode leads implanted in the region, a patient-specific anatomical model of the region and the BS electrode leads;
   populating the patient-specific anatomical model with a plurality of individual neuron models, wherein the plurality of individual neuron models respectively model an electrical response of an individual neuron to an input signal, wherein different areas of the region have different neuronal densities corresponding to different numbers of individual neurons, and wherein the plurality of individual neuron models populate the patient-specific anatomical model so that a number of the individual neuron models within respective ones of the different areas corresponds to the different numbers of individual neurons;
   constructing a patient-specific local field potential (LFP) model of the region of the brain from the populated patient-specific anatomical model and a location for each BS electrode lead of the BS electrode leads;
   determining contributions from the plurality of individual neuron models based upon a reciprocal solution from the patient-specific LFP model;
   generating an LFP signal based upon contributions from the individual neuron models at one of the BS electrode leads; and
   identifying, based on the LFP signal, a target area within the region of the brain for at least one of monitoring or treatment of a medical condition via the BS electrode leads.

2. The non-transitory computer-readable medium of claim 1, wherein the operations further comprise identifying, via the patient-specific LFP model of the region, at least one BS electrode lead of the BS electrode leads that maximizes stimulation of the target area within a selected frequency range.

3. The non-transitory computer-readable medium of claim 2, wherein the operations further comprise determining, via the patient-specific LFP model of the region, at least one optimal stimulation amplitude for stimulating the target area via the at least one BS electrode lead for the treatment of the medical condition.

4. The non-transitory computer-readable medium of claim 1, wherein the reciprocal solution is determined by applying a time varying signal to one or more of the BS electrode leads, the time varying signal triggering synaptic currents for each of the plurality of individual neuron models that give rise to the LFP signal.

5. The non-transitory computer-readable medium of claim 4, wherein the reciprocal solution applies a synchronous input to each of the plurality of individual neuron models.

6. The non-transitory computer-readable medium of claim 4, wherein the reciprocal solution applies excitatory inputs to dendritic compartments that are greater than a first distance from somas of the plurality of individual neuron models and applies inhibitory inputs to the dendritic compartments that are less than the first distance from the somas.

7. The non-transitory computer-readable medium of claim 1, wherein the radiological imaging comprises a pre-operative MRI (Magnetic Resonance Imaging) image of the region prior to implantation of the BS electrode leads and a post-operative CT (Computed Tomography) image of the region and the BS electrode leads.

8. The non-transitory computer-readable medium of claim 1, wherein each individual neuron model of the plurality of individual neuron models is a point neuron model.

9. The non-transitory computer-readable medium of claim 1, wherein the patient-specific LFP model of the region is constructed from the patient-specific anatomical model and a volume conductor model configured to model conduction through the region of the brain.

10. The non-transitory computer-readable medium of claim 1, wherein the operations further comprise determining contributions to a waveform of individual neuron models of the plurality of neuron models from the reciprocal solution.

11. An apparatus that facilitates identification of a target area of a region of a brain for treatment of a medical condition, the apparatus comprising:
   a memory configured to store radiological imaging of a region of a brain of a patient and one or more Brain Stimulation (BS) electrode leads implanted in the region of the brain; and
   one or more processors configured to:
      generate, using the radiological imaging of the region of the brain of the patient and the one or more Brain Stimulation (BS) electrode leads implanted in the region of the brain, a patient-specific anatomical model of the region and the one or more BS electrode leads;
      populate the patient-specific anatomical model with a plurality of individual neuron models, wherein the plurality of individual neuron models respectively model an electrical response of an individual neuron to an input signal, wherein different areas of the region have different neuronal densities corresponding to different numbers of individual neurons, and wherein the plurality of individual neuron models populate the patient-specific anatomical model so that a number of the individual neuron models within respective ones of the different areas corresponds to the different numbers of individual neurons;

construct a patient-specific local field potential (LFP) model of the region of the brain from the populated patient-specific anatomical model and a volume conduction model that models brain tissue in the region of the brain, the one or more BS electrode leads, and a second region surrounding the one or more BS electrode leads;

determine contributions from the plurality of individual neuron models based upon a reciprocal solution from the patient-specific LFP model;

generate an LFP signal based upon contributions from the individual neuron models at one of the BS electrode leads; and identify, based on the LFP signal, a target area within the region of the brain for at least one of monitoring or treatment of a medical condition via the one or more BS electrode leads.

12. The apparatus of claim 11, wherein the one or more processors are further configured to identify, via the patient-specific LFP model of the region, at least one BS electrode lead of the one or more BS electrode leads that maximizes stimulation of the target area within a selected frequency range.

13. The apparatus of claim 12, wherein the one or more processors are further configured to determine, via the patient-specific LFP model of the region, at least one optimal stimulation amplitude for stimulating the target area via the at least one BS electrode lead for the treatment of the medical condition.

14. The apparatus of claim 11, wherein the one or more processors are configured to identify, via the patient-specific LFP model of the region, the target area comprises determining a size and a position of the target area.

15. The apparatus of claim 14, wherein the patient-specific LFP model of the region is constructed from the patient-specific anatomical model and a location for each of a plurality of the one or more BS electrode leads.

16. The apparatus of claim 14, wherein the target area comprises a spherical region, the size is a radius of the spherical region, and the position is a center of the spherical region.

17. The apparatus of claim 11, wherein the radiological imaging comprises a pre-operative MRI (Magnetic Resonance Imaging) image of the region prior to implantation of the one or more BS electrode leads and a post-operative CT (Computed Tomography) image of the region and the one or more BS electrode leads.

18. The apparatus of claim 11, wherein each individual neuron model of the plurality of individual neuron models is a point neuron model.

19. A non-transitory computer-readable medium storing computer-executable instructions that, when executed, cause a processor to perform operations, comprising:

generating, using radiological imaging of a region of a brain of a patient and one or more Brain Stimulation (BS) electrode leads implanted in the region, a patient-specific anatomical model of the region and the one or more BS electrode leads;

voxelizing the patient-specific anatomical model to create a plurality of model sub-regions corresponding to a plurality of sub-regions of the region of the brain;

populating the plurality of model sub-regions with a plurality of individual neuron models, wherein the plurality of individual neuron models respectively model an electrical response of an individual neuron to an input signal, wherein different areas of the region have different neuronal densities corresponding to different numbers of individual neurons, and wherein the plurality of individual neuron models populate the patient-specific anatomical model so that a number of the individual neuron models within respective ones of the different areas corresponds to the different numbers of individual neurons;

constructing a patient-specific local field potential (LFP) model of the region based on the populated plurality of model sub-regions and a location for each BS electrode lead of the one or more BS electrode leads;

determining contributions from the plurality of individual neuron models based upon a reciprocal solution from the patient-specific LFP model;

generating an LFP signal based upon contributions from the individual neuron models at one of the BS electrode leads; and identifying, via the LFP signal, a size and a location of a target area within the region for at least one of monitoring or treatment of a medical condition via the one or more BS electrode leads.

20. The non-transitory computer-readable medium of claim 19, wherein the reciprocal solution is determined by applying a signal to one or more of the BS electrode leads, the signal triggering synaptic currents for each of the plurality of individual neuron models that give rise to the LFP signal.

* * * * *